United States Patent
Sorefan et al.

(10) Patent No.: US 9,909,175 B2
(45) Date of Patent: Mar. 6, 2018

(54) ANALYSING SEQUENCING BIAS

(75) Inventors: Karim Sorefan, Norwich (GB); Tamas Dalmay, Norwich (GB); Vincent Moulton, Norwich (GB); Helio Ernesto Coronel Machado Pais, Norwich (GB)

(73) Assignee: UNIVERSITY OF EAST ANGLIA, Norfolk (GB)

( * ) Notice: Subject to any disclaimer, the term of this patent is extended or adjusted under 35 U.S.C. 154(b) by 116 days.

(21) Appl. No.: 14/235,936

(22) PCT Filed: Jul. 27, 2012

(86) PCT No.: PCT/GB2012/051837
§ 371 (c)(1),
(2), (4) Date: Apr. 24, 2014

(87) PCT Pub. No.: WO2013/017861
PCT Pub. Date: Feb. 7, 2013

(65) Prior Publication Data
US 2014/0243213 A1    Aug. 28, 2014

(30) Foreign Application Priority Data

Jul. 29, 2011 (GB) .................................. 1113214.9

(51) Int. Cl.
*C12Q 1/68* (2006.01)
*C12N 15/10* (2006.01)

(52) U.S. Cl.
CPC ....... *C12Q 1/6874* (2013.01); *C12N 15/1065* (2013.01); *C12N 15/1096* (2013.01); *C12Q 1/6806* (2013.01); *C12Q 1/6809* (2013.01); *C12Q 1/6848* (2013.01); *C12Q 1/6855* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 8,192,941 B2 | 6/2012 | Kuersten | |
| 2003/0040620 A1* | 2/2003 | Langmore | C12N 15/10 536/24.3 |
| 2011/0039722 A1 | 2/2011 | Takeuchi et al. | |
| 2011/0118131 A1 | 5/2011 | Takeuchi et al. | |
| 2011/0118447 A1 | 5/2011 | Studnicka | |
| 2012/0295794 A1 | 11/2012 | Kuersten | |
| 2012/0322691 A1* | 12/2012 | Sachidanandam | C12Q 1/6855 506/16 |

FOREIGN PATENT DOCUMENTS

| | | |
|---|---|---|
| WO | 2009/088924 A2 | 7/2009 |
| WO | 2009/088928 A2 | 7/2009 |
| WO | 2009/088933 A1 | 7/2009 |
| WO | 2009/091719 A1 | 7/2009 |

OTHER PUBLICATIONS

GeneWorks (2006) "Random Hexamer Primer" Specification Sheet, www.geneworks.com/au.*
Elshire et al (2011) "A Robust, Simple Genotyping-by-Sequencing (GBS) Approach for High Diversity Species" PLoS One 6(5):e19379.*
Hafner et al. (2008)"Identification of microRNAs and other small regulatory RNAs using cDNA library sequencing" Methods 44(1):3-12.*
Clepet, Christian, "RNA Captor: A Tool for RNA Characterization", PLoS One. Apr. 13, 2011;6(4):e18445.
Perelle, S. et al., "Comparison of PCR-ELISA and LightCycler real-time PCR assays for detecting *Salmonella* spp. in milk and meat samples", Mol Cell Probes. Dec. 2004;18(6):409-20.
Shibata Y., et al. "Cloning full-length, Cap-Trapper-selected cDNAs by using the single-strand linker ligation method", Biotechniques. Jun. 2001:30(6):1250-4.
Tian, Geng, et al., "Sequencing Bias: comparison of different protocols of MicroRNA library construction", BMC Biotechnol. Sep. 6, 2010;10:64.
Vater, Axel, et al., "Short bioactive Spiegelmers to migraine-associated calcitonin gene-related peptide rapidly identified by a novel approach: Tailored-SELEX", Nucleic Acids Res. Nov. 1, 2003;31(21):e130.
Yin, Chang-Cheng et al., "Construction of a fully synthetic human scFv antibody library with CDR3 regions randomized by a split-mix-split method and its application", J Biochem. Nov. 2008;144(5):591-8.
AB Applied Biosystems, "SOLiD(tm) Small RNA Expression Kit—Small RNA Library Preparation for SOLiD(tm) Sequencing," Foster City, CA, United States, Apr. 2009, 36 pages.

* cited by examiner

*Primary Examiner* — Karen S. Weiler
(74) *Attorney, Agent, or Firm* — Robin L. Teskin; LeClairRyan, A Professional Corporation

(57) ABSTRACT

The present invention relates to methods for determining the sequence bias of a sequencing technique. Furthermore, the invention relates to methods to reduce or enhance sequence bias during sequencing of nucleic acids via techniques involving adaptor ligations. Specifically the method relates to use of a degenerate RNA sequence to analyze sequence bias when generating small RNA libraries, and to the use of modified adaptors for cloning of small RNAs with degenerate or specific sequences to reduce or enhance sequencing bias, as well as various nucleic acid molecules relating thereto or derived therefrom.

2 Claims, 29 Drawing Sheets

A. Mir-25

B. Mir-103

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: HD adaptor

<400> SEQUENCE: 1
gagatcgtat gccgtcttct gcttg                                          25

<210> SEQ ID NO 2
<211> LENGTH: 25
<212> TYPE: DNA
<213> ORGANISM: Artificial Sequence
<220> FEATURE:
<223> OTHER INFORMATION: HD Adaptor

<400> SEQUENCE: 2
attgtcgtat gccgtcttct gcttg                                          25

<210> SEQ ID NO 3
<211> LENGTH: 30
<212> TYPE: DNA
<213> ORGANISM: Artificial Sequence
<220> FEATURE:
<223> OTHER INFORMATION: 5' Adaptor
<220> FEATURE:
<221> NAME/KEY: misc_feature
<222> LOCATION: (27)..(30)
<223> OTHER INFORMATION: n is any RNA base

<400> SEQUENCE: 3
gttcagagtt ctacagtccg acgatcnnnn                                     30

<210> SEQ ID NO 4
<211> LENGTH: 26
<212> TYPE: DNA
<213> ORGANISM: Artificial Sequence
<220> FEATURE:
<223> OTHER INFORMATION: Complementary oligonucleotide

<400> SEQUENCE: 4
gatcgtcgga ctgtagaact ctgaac                                         26

<210> SEQ ID NO 5
<211> LENGTH: 28
<212> TYPE: DNA
<213> ORGANISM: Artificial Sequence
<220> FEATURE:
<223> OTHER INFORMATION: 3' Adaptor
<220> FEATURE:
<221> NAME/KEY: misc_feature
<222> LOCATION: (1)..(4)
<223> OTHER INFORMATION: n is any RNA base.

<400> SEQUENCE: 5
nnnnatctcg tatgccgtct tctgcttg                                       28

<210> SEQ ID NO 6
<211> LENGTH: 24
<212> TYPE: DNA
<213> ORGANISM: Artificial Sequence
<220> FEATURE:
<223> OTHER INFORMATION: Complementary oligonucleotide

<400> SEQUENCE: 6
caagcagaag acggcatacg agat                                                24

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: n is any base
<220> FEATURE:
<221> NAME/KEY: misc_feature
<222> LOCATION: (5)..(24)
<223> OTHER INFORMATION: n is a, c, g, or t
<220> FEATURE:
<221> NAME/KEY: misc_feature
<222> LOCATION: (25)..(25)
<223> OTHER INFORMATION: n is a fixed sequence

<400> SEQUENCE: 7 caaannnnn nnnnnnnnnn nnnnn                                                25

<210> SEQ ID NO 8
<211> LENGTH: 26
<212> TYPE: RNA
<213> ORGANISM: Artificial Sequence
<220> FEATURE:
<223> OTHER INFORMATION: Ligation adaptor

<400> SEQUENCE: 8
guucagaguu cuacaguccg acgauc                                              26

<210> SEQ ID NO 9
<211> LENGTH: 25
<212> TYPE: DNA
<213> ORGANISM: Artificial Sequence
<220> FEATURE:
<223> OTHER INFORMATION: Ligation adaptor
<220> FEATURE:
<221> NAME/KEY: misc_feature
<222> LOCATION: (1)..(1)
<223> OTHER INFORMATION: Adenosine diphosphate
<220> FEATURE:
<221> NAME/KEY: misc_feature
<222> LOCATION: (2)..(2)
<223> OTHER INFORMATION: Ribonucleotide

<400> SEQUENCE: 9
aatctcgtat gccgtcttct gcttg                                               25

<210> SEQ ID NO 10
<211> LENGTH: 30
<212> TYPE: DNA
<213> ORGANISM: Artificial Sequence
<220> FEATURE:
<223> OTHER INFORMATION: HD adaptor
<220> FEATURE:
<221> NAME/KEY: misc_feature
<222> LOCATION: (27)..(27)
<223> OTHER INFORMATION: n is any base
<220> FEATURE:
<221> NAME/KEY: misc_feature
<222> LOCATION: (28)..(30)
<223> OTHER INFORMATION: n is any RNA base

<400> SEQUENCE: 10
gttcagagtt ctacagtccg acgatcnnnn                                          30

```
<210> SEQ ID NO 11
<211> LENGTH: 26
<212> TYPE: DNA
<213> ORGANISM: Artificial Sequence
<220> FEATURE:
<223> OTHER INFORMATION: HD adaptor
<220> FEATURE:
<221> NAME/KEY: misc_feature
<222> LOCATION: (1)..(1)
<223> OTHER INFORMATION: Adenosine diphosphate
<220> FEATURE:
<221> NAME/KEY: misc_feature
<222> LOCATION: (2)..(4)
<223> OTHER INFORMATION: n is any RNA base
<220> FEATURE:
<221> NAME/KEY: misc_feature
<222> LOCATION: (5)..(5)
<223> OTHER INFORMATION: n is any base

<400> SEQUENCE: 11
annnntcgta tgccgtcttc tgcttg                                        26
```

ANALYSING SEQUENCING BIAS

PRIORITY APPLICATION INFORMATION

This application is a 35 U.S.C. 371 United States National Phase Application of PCT Application PCT/GB2012/051837, filed Jul. 27, 2012 and published as WO 2013/017861 on Feb. 7, 2013, which claims priority to United Kingdom Patent Application GB 1113214.9 filed Jul. 29, 2011, each of which is hereby incorporated by reference in its entirety herein.

FIELD OF THE INVENTION

The present invention relates to methods for determining the sequence bias of a sequencing technique. Furthermore, the invention relates to methods to reduce or enhance sequence bias during sequencing of nucleic acids via techniques involving adaptor ligations. Specifically the method relates to use of a degenerate RNA sequence to analyse sequence bias when generating small RNA libraries, and to the use of modified adaptors for cloning of small RNAs with degenerate or specific sequences to reduce or enhance sequencing bias, as well as various nucleic acid molecules relating thereto or derived therefrom.

SEQUENCE LISTING

The sequence listing in the filed named "45878o1000.txt" having a size of 3,315 bytes that was created Jan. 27, 2014 is hereby incorporated by reference in its entirety.

BACKGROUND OF THE INVENTION

Many molecular biological methods require a cloning step which requires the use of a DNA or RNA ligase to attach oligonucleotide adaptors or other sequences to a target nucleotide sequence. The efficiency of this ligation is dependent on the sequence of the adaptor and the target. When creating a library of sequences from RNA or DNA it is often important to ligate all possible sequences and also for the library to be representative of the relative abundance of the target. These two properties are important when generating high quality libraries of small RNAs. These libraries can be sequenced using traditional Sanger sequencing but are now more commonly sequenced by high throughput sequencing or Next Generation Sequencing (NGS) techniques.

Eukaryotic gene expression is regulated at several layers and one of the most recently discovered mechanisms involves small, 20-24 nucleotide (nt) long, non-coding RNA molecules (sRNAs) (Fire, Xu et al. 1998; Voinnet 2002). There are several classes of sRNAs with different biogenesis pathways and modes of action. The best characterised class are the microRNAs (miRNAs) that are generated from stem-loop structures and target mRNAs in trans. Most miRNAs are expressed specifically in certain tissues and at specific developmental stages and their accumulation often changes due to external cues and during disease (MicroR-NAs in Cancer Translational Research, William C. S. Cho, 2011, Springer). Several databases have compiled the association of miRNAs and disease including the human microRNA disease database and mir2disease (www.mir2disease.org/; 202.38.126.151/hmdd/mirna/md/) and new products have recently been launched to classify cancers (or diseases) based on their miRNA profiles, such as Mirview (Rosetta Genomics, US 2010/0273172).

Therefore, accurately profiling the level of miRNAs (and other classes of sRNAs) is very important in both basic and clinical research. Identifying an interesting miRNA for further study is an empirical process that is often based on its high expression and clear differential expression. These criteria are more important when the biological context of the miRNA is lacking such as in animals where target prediction is poor (Dalmay 2008). In addition, expression level is often used to discern between the miRNA and miRNA star. Accurate miRNA profiling is complicated by the heterogeneous nature of miRNAs such as sequence isoforms and length isomirs since these are thought to have differential activities (Fernandez-Valverde, Taft et al. 2010; Guo and Lu 2010; Starega-Roslan, Krol et al. 2011).

Measuring microRNAs with sequencing technologies such as high throughput and Sanger or by quantitative PCR (QPCR) requires the use of nucleic acid modifying enzymes. Ligases, reverse transcriptases and DNA polymerases are some of the most important enzymes used in molecular biology. To improve the activity of these enzymes their function needs to be fully understood, which requires a method of measuring their activity and identifying the determinants that regulate their function.

SUMMARY OF THE INVENTION

In a first aspect, the present invention provides a method for determining the sequence bias of a sequencing technique, the method comprising:
  (a) providing a degenerate library of nucleic acid molecules;
  (b) determining the sequence of the nucleic acid molecules in the degenerate library of nucleic acid molecules provided in (a) using the sequencing technique; and
  (c) analysing the sequencing results to determine over- or under-representation of particular nucleic acid molecules.

Preferably, the sequencing technique involves ligation of adaptor molecules to the 5', 3' or 5' and 3' ends of the nucleic acid molecules in the degenerate library of nucleic acid molecules.

In a preferred embodiment, the method according to the invention, comprises:
  (a) providing a degenerate library of nucleic acid molecules;
  (b) ligating an oligonucleotide of known sequence with a blocked 3' end (3' adaptor molecule) to the 3' ends of the nucleic acid molecules using a ligase;
  (c) ligating an oligonucleotide of known sequence with a blocked 5' end (5' adaptor molecule) to the 5' ends of the nucleic acid molecules from step (b) using a ligase;
  (d) sequencing the resulting library of ligated nucleic acid molecules; and
  (e) analysing the sequencing results to determine over- or under-representation of particular nucleic acid molecules;
wherein steps (b) and (c) may be carried out in any order.

In another preferred embodiment, the method according to the invention, comprises:
  (a) providing a degenerate library of nucleic acid molecules, wherein the nucleic acid molecules have a consistent 3' region and a blocked 3' end;
  (b) ligating an oligonucleotide of known sequence with a blocked 5' end (5' adaptor molecule) to the 5' ends of the nucleic acid molecules from step (a) using a ligase;

(c) sequencing the resulting amplified library of nucleic acid molecules; and
(d) analysing the sequencing results to determine over- or under-representation of particular nucleic acid molecules.

In a further preferred embodiment, the method according to the invention, comprises:
(a) providing a degenerate library of nucleic acid molecules, wherein the nucleic acid molecules have a consistent 5' region and a blocked 5' end;
(b) ligating an oligonucleotide of known sequence with a blocked 3' end (3' adaptor molecule) to the 3' ends of the nucleic acid molecules from step (a) using a ligase;
(c) sequencing the resulting amplified library of nucleic acid molecules; and
(d) analysing the sequencing results to determine over- or under-representation of particular nucleic acid molecules.

In yet another preferred embodiment, the method according to the invention, comprises:
(a) providing a degenerate library of nucleic acid molecules, wherein the nucleic acid molecules have a consistent 5' region and a consistent 3' region;
(b) sequencing the resulting amplified library of nucleic acid molecules; and
(c) analysing the sequencing results to determine over- or under-representation of particular nucleic acid molecules.

In still another preferred embodiment, the method according to the invention, comprises:
(a) providing a degenerate library of RNA molecules;
(b) ligating an oligonucleotide of known sequence with a blocked 3' end (3' adaptor molecule) to the 3' ends of the RNA molecules using a ligase;
(c) ligating an oligonucleotide of known sequence with a blocked 5' end (5' adaptor molecule) to the 5' ends of the RNA molecules from step (b) using a ligase;
(d) reverse transcribing the RNA molecules into cDNA using a reverse transcriptase and a primer capable of hybridising to the 3' adaptor molecule;
(e) if necessary, creating an amplified library of nucleic acid molecules by PCR of the cDNA molecules obtained in step (d) using a primer capable of hybridising to the complement of the 5' adaptor molecule and a primer capable of hybridising to the 3' adaptor molecule;
(d) sequencing the resulting library of nucleic acid molecules; and
(e) analysing the sequencing results to determine over- or under-representation of particular nucleic acid molecules;
wherein steps (b) and (c) may be carried out in any order.

In a yet further preferred embodiment, the method according to the invention, comprises:
(a) providing a degenerate library of DNA molecules;
(b) ligating an oligonucleotide of known sequence with a blocked 3' end (3' adaptor molecule) to the 3' ends of the DNA molecules using a ligase;
(c) ligating an oligonucleotide of known sequence with a blocked 5' end (5' adaptor molecule) to the 5' ends of the DNA molecules from step (b) using a ligase;
(d) amplifying the ligated DNA molecules by asymmetric PCR;
(e) if necessary, creating an amplified library of nucleic acid molecules by PCR of the DNA molecules obtained in step (d) using a primer capable of hybridising to the complement of the 5' adaptor molecule and a primer capable of hybridising to the 3' adaptor molecule;
(d) sequencing the resulting library of nucleic acid molecules; and
(e) analysing the sequencing results to determine over- or under-representation of particular nucleic acid molecules;
wherein steps (b) and (c) may be carried out in any order.

In another aspect, the present invention provides a method of reducing the sequence bias of a sequencing technique involving adaptor ligation, the method comprising:
(a) providing a set of oligonucleotides of known sequence with blocked 3' ends (3' adaptor molecules) and a set of oligonucleotides of known sequence with blocked 5' ends (5' adaptor molecules), wherein the 3' and 5' adaptor molecules comprise one or more degenerate nucleotides;
(b) ligating the 3' adaptor molecules to the 3' ends of the target nucleic acid molecules using a ligase;
(c) ligating the 5' adaptor molecules to the 5' ends of the target nucleic acid molecules from step (b) using a ligase; and
(d) determining the sequence of the target nucleic acid molecules obtained in step (c) using a primer capable of hybridising to the complement of the 5' adaptor molecule and a primer capable of hybridising to the 3' adaptor molecule.

In yet another aspect, the present invention provides a method of preferentially detecting a target nucleic acid molecule in a library of nucleic acid molecules, the method comprising:
(a) providing a set of oligonucleotides of known sequence with blocked 3' ends (3' adaptor molecules) and a set of oligonucleotides of known sequence with blocked 5' ends (5' adaptor molecules), wherein the 3' and 5' adaptor molecules comprise one or more degenerate nucleotides and are preferentially ligatable to the target nucleic acid molecule;
(b) ligating the 3' adaptor molecule to the 3' ends of the nucleic acid molecules in the library of nucleic acid molecules using a ligase;
(c) ligating the 5' adaptor molecule to the 5' ends of nucleic acid molecules from step (b) using a ligase;
(d) creating an amplified library of nucleic acid molecules by PCR of the nucleic acid molecules obtained in step (c) using a primer capable of hybridising to the complement of the 5' adaptor molecule and a primer capable of hybridising to the 3' adaptor molecule;
(e) sequencing the resulting amplified library of nucleic acid molecules; and
(f) analysing the sequencing results to determine whether the target nucleic acid molecule is present in the library of nucleic acid molecules.

In still another aspect, the present invention provides a method of preferentially detecting a target nucleic acid molecule in a library of nucleic acid molecules, the method comprising:
(a) providing an oligonucleotide of known sequence (adaptor molecule), comprising one or more degenerate nucleotides, wherein said oligonucleotide is preferentially ligatable to the target nucleic acid molecule;
(b) ligating the adaptor molecule to the nucleic acid molecules in the library using a ligase;
(c) performing quantitative PCR on the molecules obtained in step (b) using one primer specific for the adaptor molecule and one primer specific for the target nucleic acid.

Preferably, the target nucleic acid is associated with a disease or pre-disease state. Preferably, the target nucleic acid is associated with a particular organism.

Preferably, the target nucleic acid is associated with a particular tissue type. Preferably, the target nucleic acid is associated with a particular developmental stage.

In preferred embodiments of the aspects described above, the nucleic acid molecules are RNA molecules. In other preferred embodiments of the aspects described above, the nucleic acid molecules are DNA molecules.

In another aspect, the present invention provides a method of generating a cDNA library from a library of RNA molecules, the method comprising:
(a) providing a set of oligonucleotides of known sequence with blocked 3' ends (3' adaptor molecules) and a set of oligonucleotides of known sequence with blocked 5' ends (5' adaptor molecules), wherein the 3' and 5' adaptor molecules comprise one or more degenerate nucleotides;
(b) ligating the 3' adaptor molecules to the 3' ends of the RNA molecules using a ligase;
(c) ligating the 5' adaptor molecules to the 5' ends of the RNA molecules from step (b) using a ligase;
(d) creating hybrid RNA/DNA template molecules from the RNA molecules obtained in step (c) using a reverse transcriptase enzyme and a primer capable of hybridising to the 3' adaptor molecule; and
(e) creating a cDNA library by PCR of the hybrid RNA/DNA template molecules obtained in step (d) using a primer capable of hybridising to the complement of the 5' adaptor molecule and a primer capable of hybridising to the 3' adaptor molecule.

Oligonucleotides of known sequence with blocked 3' ends (3' adaptor molecules) and oligonucleotides of known sequence with blocked 5' ends (5' adaptor molecules), containing one or more degenerate nucleotides are also referred to herein as High Definition (HD) adaptors.

In another aspect, the present invention provides a set of oligonucleotides of known sequence with blocked 3' ends (3' adaptor molecules) and/or a set of oligonucleotides of known sequence with blocked 5' ends (5' adaptor molecules), wherein the 3' and 5' adaptor molecules comprise one or more degenerate nucleotides, for use in the methods described herein.

In a further aspect, the present invention provides a set of oligonucleotides of known sequence with blocked 3' ends (3' adaptor molecules) and/or a set of oligonucleotides of known sequence with blocked 5' ends (5' adaptor molecules), wherein the 3' and 5' adaptor molecules comprise one or more degenerate nucleotides, wherein said oligonucleotides are preferentially ligatable to a target sequence, for use in the methods described herein.

In preferred embodiments, the oligonucleotides described in the above aspects may have 1, 2, 3, 4, 5, 6 or more degenerate nucleotides. The degenerate nucleotides may be grouped at the 3', 5' or central regions of the oligonucleotide. Alternatively, they may be distributed along the length of the oligonucleotide in any configuration.

DESCRIPTION OF THE DRAWINGS

The present invention will be further understood by reference to the attached drawings, in which.

DETAILED DESCRIPTION

Figure 1:
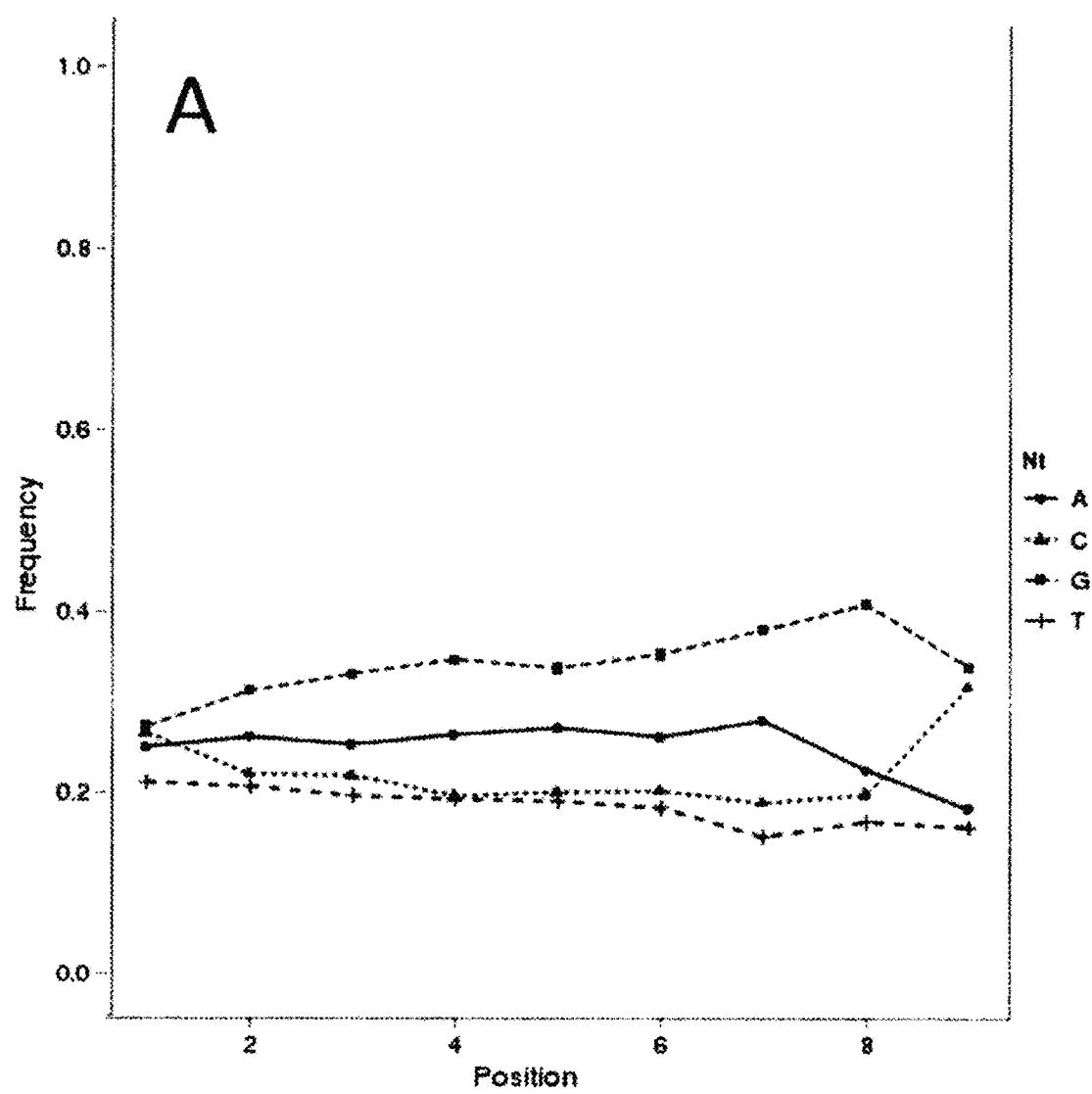
FIG. 1: Analysis of sequence data from N9 (a completely degenerated RNA oligonucleotide consisting of nine N nucleotides where N is either A, C, G or U with 25% chance for each nucleotide) synthetic samples. A-C. Nucleotide frequency plots showing proportion of each nucleotide at each position in the sequence. A. Illumina adaptors show large bias for sequences with the nucleotide Guanine at position 8, which illustrates the bias problem. B. HD adaptors have significantly reduced bias and lines are close to the theoretical optimum of 0.25 frequency. C. 'No ligation' sample shows bias caused by PCR of the oligonucleotides. PCR bias was almost zero with lines at the theoretical optimum of 0.25 frequency.
Figure 1:
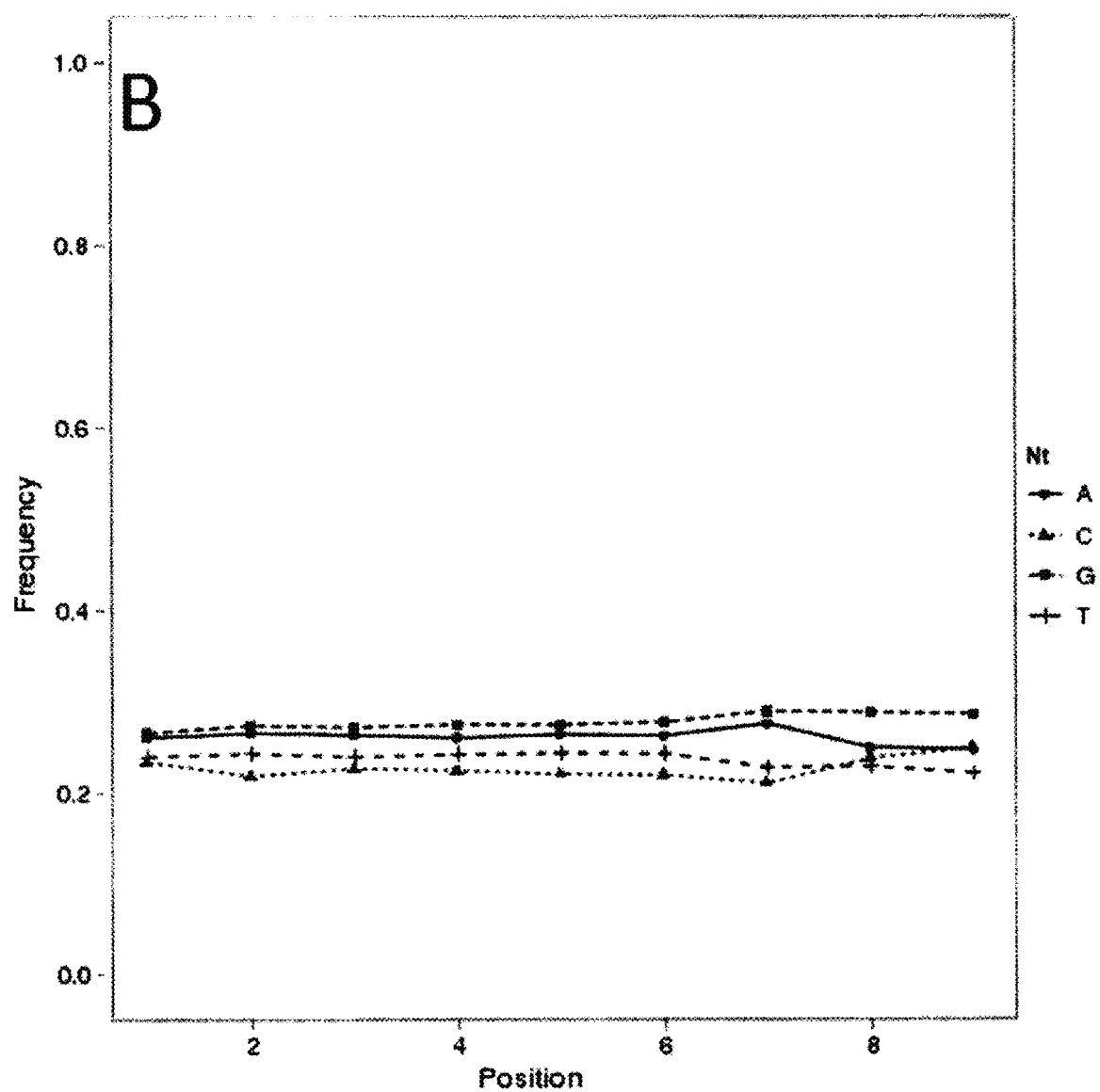
Figure 1:
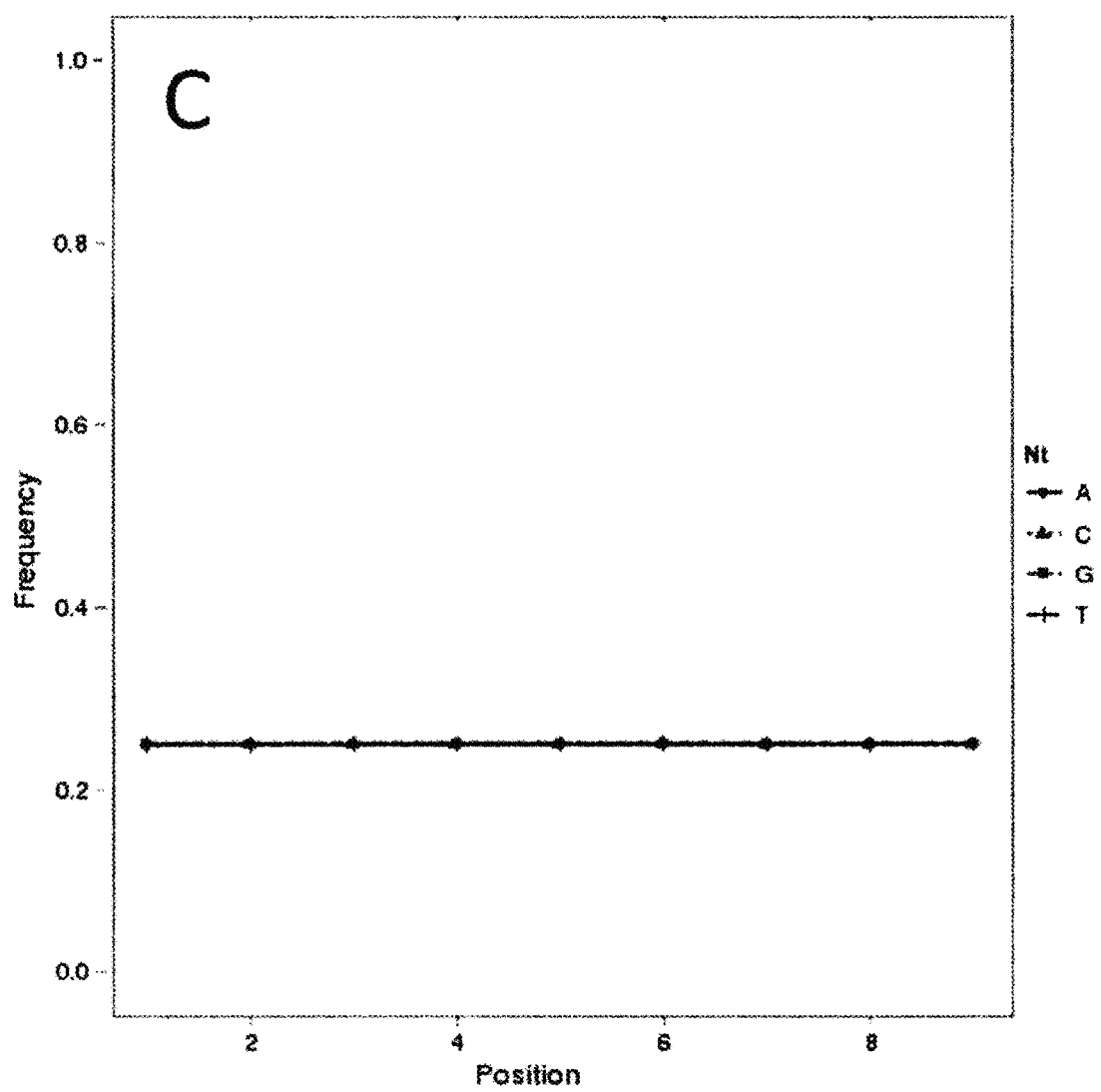

High-throughput sequencing technologies are ideal candidates for profiling sRNAs because they have the ability to identify previously un-annotated sRNAs and quantify their accumulation level. The assumption is that the number of times a certain short read is found is correlated with the accumulation level of the sRNA in the cells. However, recently the present inventors and others (Tian, Yin et al. 2010; Linsen, de Wit et al. 2009; Willenbrock, Salomon et al. 2009, McCormick, Willmann et al. 2011, Hafner et al 2011) found that different library preparation protocols have preferences for certain types of short sequences, which leads to inaccurate sRNA profiles. Some sequences are found more often than would be expected, some sequences are found less frequently than expected and maybe some sequences are not found at all despite the fact they are present in the cells. If severe over-representation of some sequences was observed in biological data it would reduce the average representation of other sequences. Therefore, the potential for sequencing low abundance small RNAs would be reduced and raises the possibility that some small RNAs are 'unclonable' using standard protocol and yet to be identified. Therefore, there is a requirement for more efficient and effective methods for generating unbiased cloning libraries for high-throughput or other sequencing methods.

Accordingly, the present invention provides, in a first aspect, a method for determining the sequence bias of a sequencing technique, the method comprising:
(a) providing a degenerate library of nucleic acid molecules;
(b) determining the sequence of the nucleic acid molecules in the degenerate library of nucleic acid molecules provided in (a) using the sequencing technique; and
(c) analysing the sequencing results to determine over- or under-representation of particular nucleic acid molecules.

The meaning of the term "degenerate library" will be clear to those of skill in the art. Generally, it should be taken to mean a group of nucleic acid molecules in which every possible combination of nucleotides is represented. Typically, although not always, the library will be of oligonucleotides of a given length. For example, a degenerate library of dinucleotide molecules has 16 members: AA; AG; AC; AT; GA; GG; GC; GT; TA; TG; TC; TT; CA; CG; CC; and CT. The number of members in a degenerate library of fixed length is given by the formula $4^L$, where L is the length of the oligonucleotide. Similarly, the term "degenerate nucleotide" will be clear to those of skill in the art. Where an oligonucleotide is described as having a degenerate nucleotide at a particular position, the skilled person will appreciate that this refers to a group of oligonucleotides having either A, G, C, or T at the degenerate position, each present at approximately equal concentration. The number of discrete oligonucleotides is given by the formula $4^n$, where n is the number of degenerate nucleotides in the sequence. Thus, an oligonucleotide having four degenerate positions is in fact a group of 256 unique oligonucleotides. Usually, each oligonucleotide will be present at approximately equal concentration. Furthermore, the skilled person will appreciate that in the case of RNA 'T' may be replaced by 'U'.

The meaning of the term "ligating" will be clear to those of skill in the art and has a consistent meaning throughout the present application. Generally, it is intended to encompass the covalent linking of two nucleic acid molecules via phosphodiester bonds. Usually, this is achieved via the use of a ligase enzyme, including but not limited to DNA ligases I to IV or T4 RNA ligase 1 or 2. Optimum conditions for ligation of nucleic acids will be known to those of skill in the art.

The terms "blocked 5' end" and "blocked 3' end" are intended to indicate that the molecule is not capable of having another nucleic molecule joined or ligated to its 5' or 3' end, respectively. Methods of achieving this will be known to those of skill in the art and include, but are not limited to, the use of a nucleotide diphosphate in the 5' or 3' position. The meaning of these terms is consistent throughout the present application.

The meaning of the phrase "capable of hybridising to" will be clear to those of skill in the art and has a consistent meaning throughout the present application. Generally, it is intended to encompass the conditions found during the annealing step of a typical PCR or Reverse Transcriptase PCR (rtPCR). The degree of hybridisation need only be sufficient to ensure that the polymerase chain reaction takes place and need not be over the entire length of the target region. As will be appreciated by the skilled person, an oligonucleotide may contain a number of mismatches and still be considered capable of hybridising to a particular target. The conditions encountered during the annealing steps of a PCR will be generally known to one skilled in the art, although the precise annealing conditions will vary from reaction to reaction (see Sambrook et al., 2001, Molecular Cloning, A Laboratory Manual, 3rd Ed, Cold Spring Harbor Laboratory Press, NY; Current Protocols, eds Ausubel et al.). Typically such conditions may comprise, but are not limited to, (following a denaturing step at a temperature of about 94° C. for about one minute) exposure to a temperature in the range of from 40° C. to 72° C. (preferably 50-68° C.) for a period of about 1 minute in standard PCR reaction buffer.

Preferably, the sequencing technique involves ligation of adaptor molecules to the 5', 3' or 5' and 3' ends of the nucleic acid molecules in the degenerate library of nucleic acid molecules.

In a preferred embodiment, the method according to the invention, comprises:
(a) providing a degenerate library of nucleic acid molecules;
(b) ligating an oligonucleotide of known sequence with a blocked 3' end (3' adaptor molecule) to the 3' ends of the nucleic acid molecules using a ligase;
(c) ligating an oligonucleotide of known sequence with a blocked 5' end (5' adaptor molecule) to the 5' ends of the nucleic acid molecules from step (b) using a ligase;
(d) sequencing the resulting library of ligated nucleic acid molecules; and
(e) analysing the sequencing results to determine over- or under-representation of particular nucleic acid molecules;
wherein steps (b) and (c) may be carried out in any order.

In another preferred embodiment, the method according to the invention, comprises:
(a) providing a degenerate library of nucleic acid molecules, wherein the nucleic acid molecules have a consistent 3' region and a blocked 3' end;
(b) ligating an oligonucleotide of known sequence with a blocked 5' end (5' adaptor molecule) to the 5' ends of the nucleic acid molecules from step (a) using a ligase;
(c) sequencing the resulting amplified library of nucleic acid molecules; and
(d) analysing the sequencing results to determine over- or under-representation of particular nucleic acid molecules.

In a further preferred embodiment, the method according to the invention, comprises:
(a) providing a degenerate library of nucleic acid molecules, wherein the nucleic acid molecules have a consistent 5' region and a blocked 5' end;
(b) ligating an oligonucleotide of known sequence with a blocked 3' end (3' adaptor molecule) to the 3' ends of the nucleic acid molecules from step (a) using a ligase;
(c) sequencing the resulting amplified library of nucleic acid molecules; and
(d) analysing the sequencing results to determine over- or under-representation of particular nucleic acid molecules.

In yet another preferred embodiment, the method according to the invention, comprises:
(a) providing a degenerate library of nucleic acid molecules, wherein the nucleic acid molecules have a consistent 5' region and a consistent 3' region;
(b) sequencing the resulting amplified library of nucleic acid molecules; and
(c) analysing the sequencing results to determine over- or under-representation of particular nucleic acid molecules.

In still another preferred embodiment, the method according to the invention, comprises:
(a) providing a degenerate library of RNA molecules;
(b) ligating an oligonucleotide of known sequence with a blocked 3' end (3' adaptor molecule) to the 3' ends of the RNA molecules using a ligase;
(c) ligating an oligonucleotide of known sequence with a blocked 5' end (5' adaptor molecule) to the 5' ends of the RNA molecules from step (b) using a ligase;
(d) reverse transcribing the RNA molecules into cDNA using a reverse transcriptase and a primer capable of hybridising to the 3' adaptor molecule;
(e) if necessary, creating an amplified library of nucleic acid molecules by PCR of the cDNA molecules obtained in step (d) using a primer capable of hybridising to the complement of the 5' adaptor molecule and a primer capable of hybridising to the 3' adaptor molecule;
(d) sequencing the resulting library of nucleic acid molecules; and
(e) analysing the sequencing results to determine over- or under-representation of particular nucleic acid molecules;
wherein steps (b) and (c) may be carried out in any order.

In a yet further preferred embodiment, the method according to the invention, comprises:
(a) providing a degenerate library of DNA molecules;
(b) ligating an oligonucleotide of known sequence with a blocked 3' end (3' adaptor molecule) to the 3' ends of the DNA molecules using a ligase;
(c) ligating an oligonucleotide of known sequence with a blocked 5' end (5' adaptor molecule) to the 5' ends of the DNA molecules from step (b) using a ligase;
(d) amplifying the ligated DNA molecules by asymmetric PCR;
(e) if necessary, creating an amplified library of nucleic acid molecules by PCR of the DNA molecules obtained in step (d) using a primer capable of hybridising to the complement of the 5' adaptor molecule and a primer capable of hybridising to the 3' adaptor molecule;
(d) sequencing the resulting library of nucleic acid molecules; and
(e) analysing the sequencing results to determine over- or under-representation of particular nucleic acid molecules;
wherein steps (b) and (c) may be carried out in any order.

In another aspect, the present invention provides a method of reducing the sequence bias of a sequencing technique involving adaptor ligation, the method comprising:
(a) providing a set of oligonucleotides of known sequence with blocked 3' ends (3' adaptor molecules) and a set of oligonucleotides of known sequence with blocked 5' ends (5' adaptor molecules), wherein the 3' and 5' adaptor molecules comprise one or more degenerate nucleotides;

(b) ligating the 3' adaptor molecules to the 3' ends of the target nucleic acid molecules using a ligase;

(c) ligating the 5' adaptor molecules to the 5' ends of the target nucleic acid molecules from step (b) using a ligase; and (d) determining the sequence of the target nucleic acid molecules obtained in step (c) using a primer capable of hybridising to the complement of the 5' adaptor molecule and a primer capable of hybridising to the 3' adaptor molecule.

In yet another aspect, the present invention provides a method of preferentially detecting a target nucleic acid molecule in a library of nucleic acid molecules, the method comprising:

(a) providing a set of oligonucleotides of known sequence with blocked 3' ends (3' adaptor molecules) and a set of oligonucleotides of known sequence with blocked 5' ends (5' adaptor molecules), wherein the 3' and 5' adaptor molecules comprise one or more degenerate nucleotides and are preferentially ligatable to the target nucleic acid molecule;

(b) ligating the 3' adaptor molecule to the 3' ends of the nucleic acid molecules in the library of nucleic acid molecules using a ligase;

(c) ligating the 5' adaptor molecule to the 5' ends of nucleic acid molecules from step (b) using a ligase;

(d) creating an amplified library of nucleic acid molecules by PCR of the nucleic acid molecules obtained in step (c) using a primer capable of hybridising to the complement of the 5' adaptor molecule and a primer capable of hybridising to the 3' adaptor molecule;

(e) sequencing the resulting amplified library of nucleic acid molecules; and (f) analysing the sequencing results to determine whether the target nucleic acid molecule is present in the library of nucleic acid molecules.

In still another aspect, the present invention provides a method of preferentially detecting a target nucleic acid molecule in a library of nucleic acid molecules, the method comprising:

(a) providing an oligonucleotide of known sequence (adaptor molecule), comprising one or more degenerate nucleotides, wherein said oligonucleotide is preferentially ligatable to the target nucleic acid molecule;

(b) ligating the adaptor molecule to the nucleic acid molecules in the library using a ligase;

(c) performing quantitative PCR on the molecules obtained in step (b) using one primer specific for the adaptor molecule and one primer specific for the target nucleic acid.

Preferably, the target nucleic acid is associated with a disease or pre-disease state. Preferably, the target nucleic acid is associated with a particular organism. Preferably, the target nucleic acid is associated with a particular tissue type. Preferably, the target nucleic acid is associated with a particular developmental stage.

In preferred embodiments of the aspects described above, the nucleic acid molecules are RNA molecules. In other preferred embodiments of the aspects described above, the nucleic acid molecules are DNA molecules.

In another aspect, the present invention provides a method of generating a cDNA library from a library of RNA molecules, the method comprising:

(a) providing a set of oligonucleotides of known sequence with blocked 3' ends (3' adaptor molecules) and a set of oligonucleotides of known sequence with blocked 5' ends (5' adaptor molecules), wherein the 3' and 5' adaptor molecules comprise one or more degenerate nucleotides;

(b) ligating the 3' adaptor molecules to the 3' ends of the RNA molecules using a ligase;

(c) ligating the 5' adaptor molecules to the 5' ends of the RNA molecules from step (b) using a ligase;

(d) creating hybrid RNA/DNA template molecules from the RNA molecules obtained in step (c) using a reverse transcriptase enzyme and a primer capable of hybridising to the 3' adaptor molecule; and (e) creating a cDNA library by PCR of the hybrid RNA/DNA template molecules obtained in step (d) using a primer capable of hybridising to the complement of the 5' adaptor molecule and a primer capable of hybridising to the 3' adaptor molecule.

In another aspect, the present invention provides a set of oligonucleotides of known sequence with blocked 3' ends (3' adaptor molecules) and/or a set of oligonucleotides of known sequence with blocked 5' ends (5' adaptor molecules), wherein the 3' and 5' adaptor molecules comprise one or more degenerate nucleotides, for use in the methods described herein.

In a further aspect, the present invention provides a set of oligonucleotides of known sequence with blocked 3' ends (3' adaptor molecules) and/or a set of oligonucleotides of known sequence with blocked 5' ends (5' adaptor molecules), wherein the 3' and 5' adaptor molecules comprise one or more degenerate nucleotides, wherein said oligonucleotides are preferentially ligatable to a target sequence, for use in the methods described herein.

In preferred embodiments, the oligonucleotides described in the above aspects may have 1, 2, 3, 4, 5, 6 or more degenerate nucleotides. The degenerate nucleotides may be grouped at the 3', 5' or central regions of the oligonucleotide. Alternatively, they may be distributed along the length of the oligonucleotide in any configuration.

The present inventors set out to evaluate the sequence preference for library preparation for high-throughput sequencing, focussing on the Illumina small RNA cloning protocol since this is most often used platform for sRNAs. Instead of testing the preference for known miRNAs (Linsen, de Wit et al. 2009; Willenbrock, Salomon et al. 2009) the present inventors developed a novel assay to test all possible sequences in order to understand the reason behind the preference. Therefore, the present inventors generated cDNA libraries using two completely degenerated 21 mer RNA oligonucleotides (N21), which contained either Adenosine (A), Guanine (G), Cytosine (C) or Uracil (U) at each position with a 25% chance for each types of nucleotides as each sequence is presumed to be synthesised at equal concentration (two independent batches of N21 were used to minimise the risk of bias during synthesis). The N21 oligonucleotides are ligated to an adaptor with a pre-adenylated 5' end and a blocked 3' end so this adaptor (3' adaptor) can only ligate to the 3' end of the N21 oligonucleotide. Then the ligation products are ligated to a different adaptor (5' adaptor) which has a blocked 5' end and a 3' hydroxyl end. These ligation products are then used as templates in a reverse transcription reaction initiated with a primer complementary to the 3' adaptor followed by a PCR reaction using primers that can anneal to the 5' and 3' adaptors, respectively. The PCR products are then sequenced on the Illumina GAII platform. If there was no sequence bias, after the PCR step all sequences should be present in the library a similar number of times. However, since the number of possible sequences in the N21 library is 4,398 trillion and only about 20-25 million reads can be completed, many sequences cannot be sequenced at all and there will only be 1-2 reads for those that are sequenced. To overcome this problem the present inventors also generated a library for a 9mer degenerated RNA oligonucleotide (N9), which contains 262,144 different sequences. Therefore, a significant read number can be expected for each sequence if there was no sequence bias. All three degenerated oligonucleotides (two N21 and one N9) were used to generate two independent libraries.

In parallel to the these 'ligation experiments', the present inventors investigated the baseline nucleotide bias caused by PCR and the sequencing machine. A DNA oligonucleotide pool was synthesised that simulated a cloned and reverse transcribed miRNA. This sequence included a 5' adaptor sequence, central 21 N degenerate sequence and 3' adaptor sequence. After PCR amplification the products were sequenced.

Results

Figure 2:
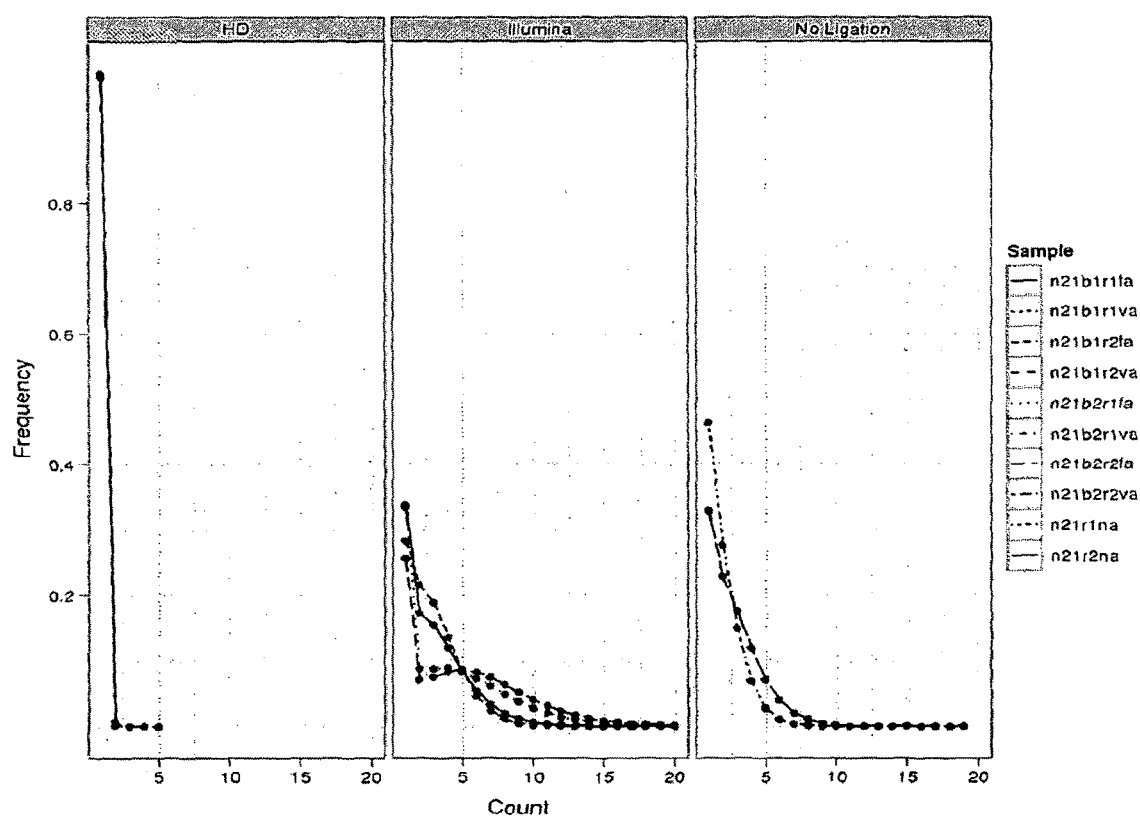
FIG. 2: Analysis of sequence data from N21 (a completely degenerated RNA oligonucleotide consisting of nine N nucleotides where N is either A, C, G or U with 25% chance for each nucleotide) synthetic samples. A. The proportion of reads with a particular count number. The HD and Illumina was performed with two independent synthetic RNAs and sequenced in duplicate. The 'no ligation' sample was sequenced in duplicate. The theoretical optimum is one count per sequence. Over 95% of sequences were found only once in the HD adaptor sample. The Illumina adaptors favoured some sequences resulting in multiple reads of the same sequence. B-D Nucleotide frequency plots showing proportion of each nucleotide at each position in the sequence. B. As an illustration of sequencing bias, Illumina adaptors show large bias for sequences with the nucleotide Guanine at position 20. C. HD adaptors have significantly reduced bias and lines are closer to the theoretical optimum of 0.25 frequency. D. 'No ligation' sample shows bias caused by PCR of the oligonucleotides. Sequences with high Guanine and Adenosine nucleotide composition are preferentially amplified and sequenced.
Figure 2:
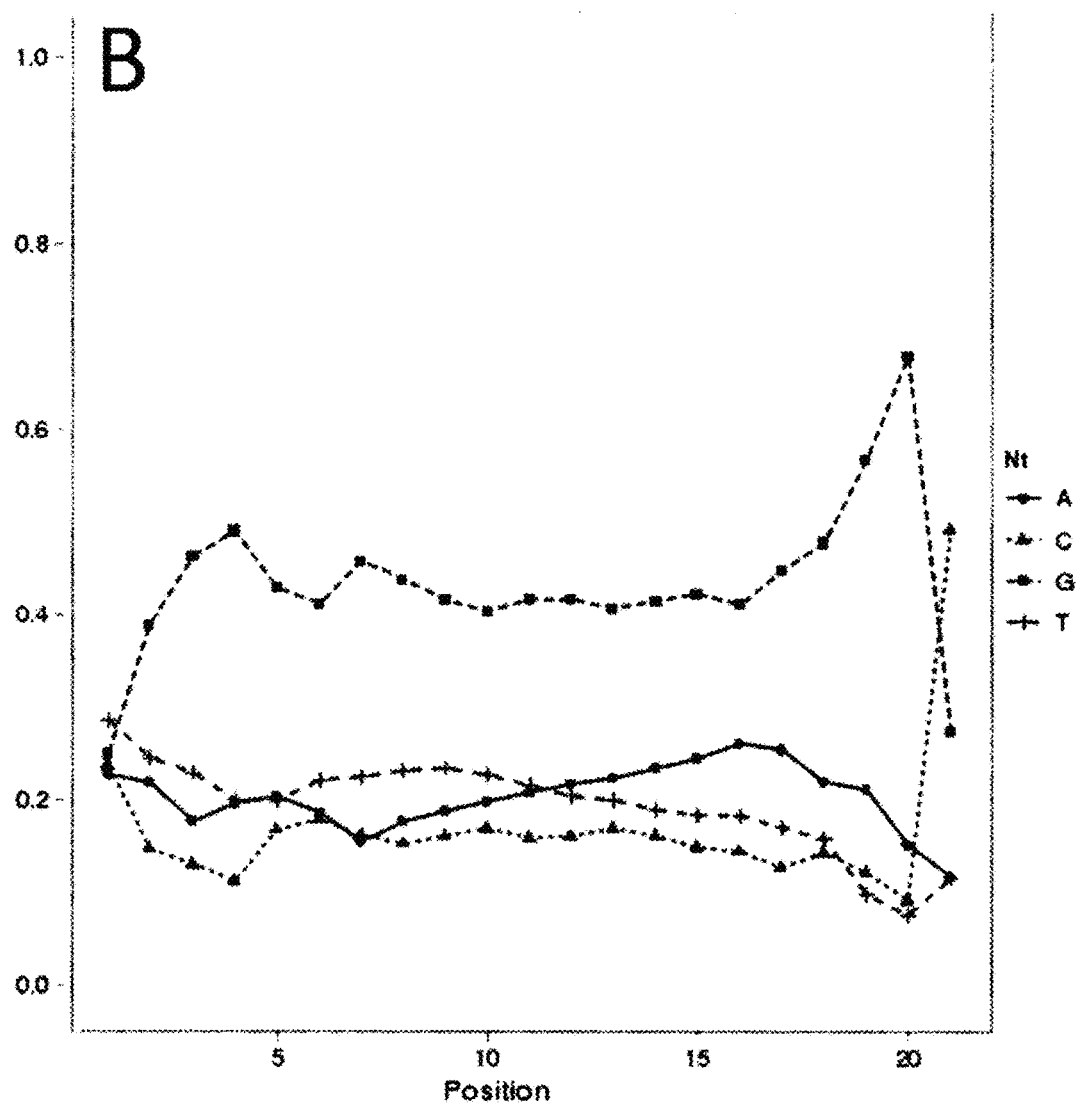
Figure 2:
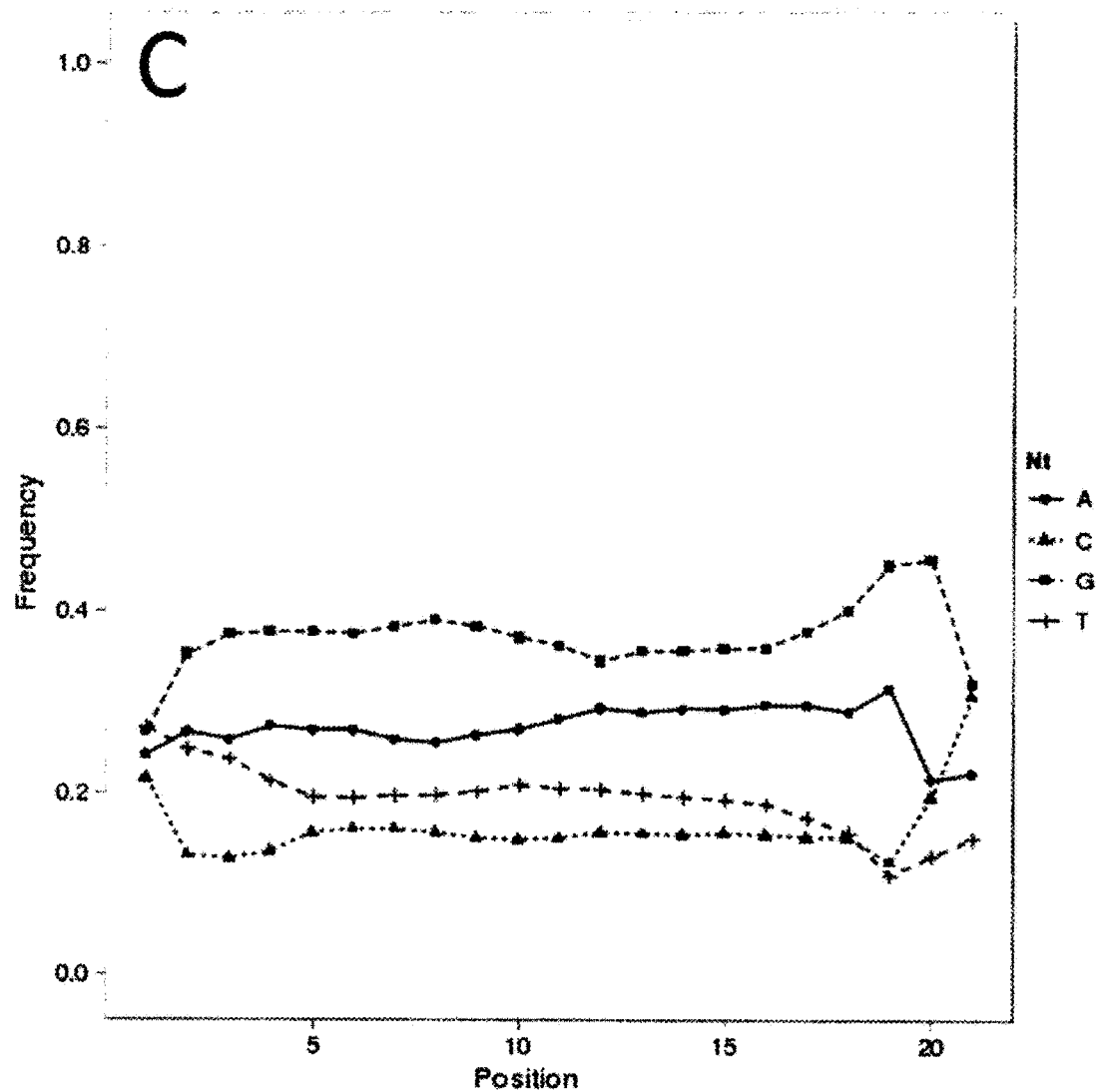
Figure 2:
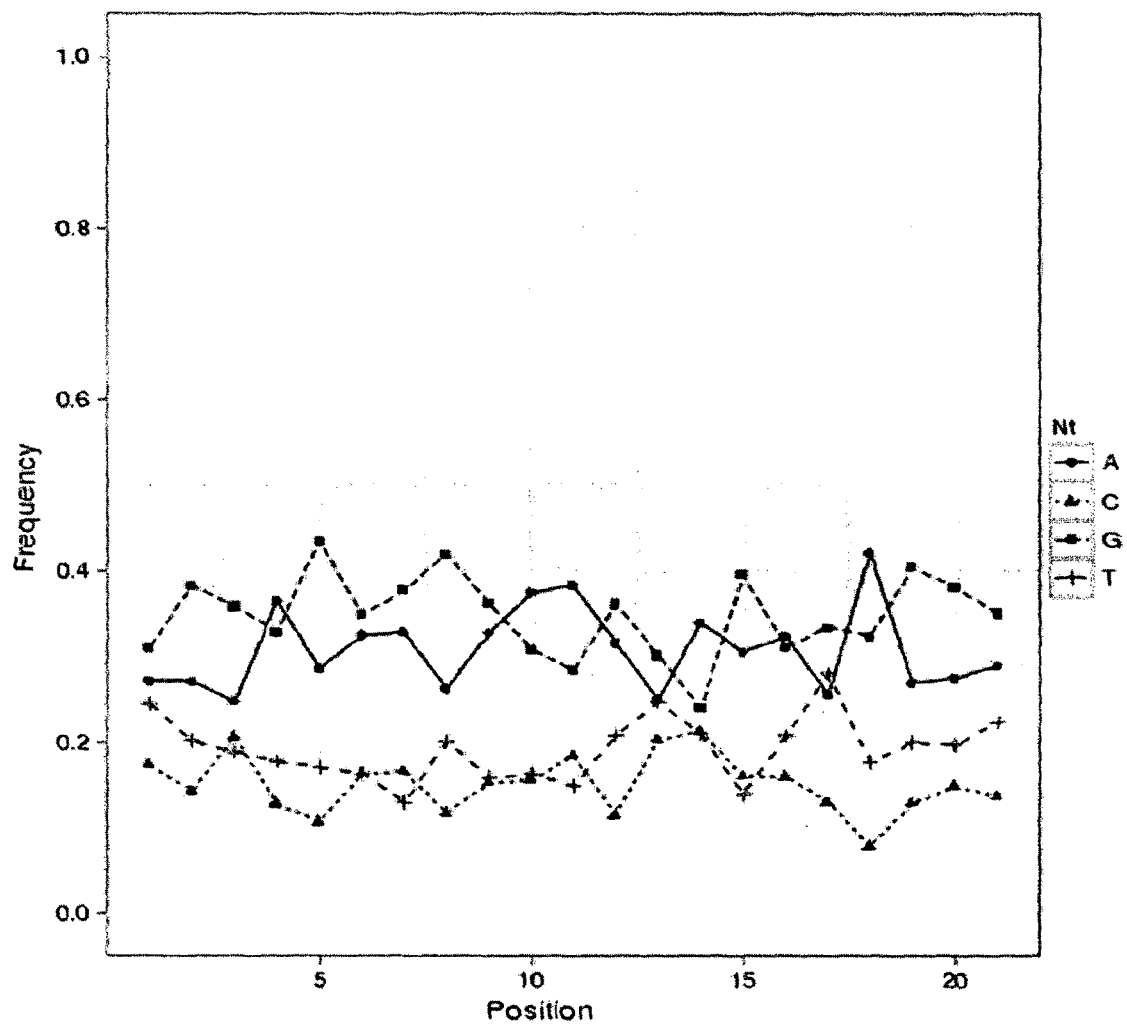

The Illumina adaptors were not uniform when cloning small RNAs. The reads obtained for the N9 Illumina adaptor libraries did not show a uniform distribution across all possible sequences. In fact, 56% of the possible sequences were not found at all and the reads showed very strong position-specific nucleotide bias (FIG. 1A). The N21 libraries also showed very strong bias: 35 sequences were found more than 100 times and 548 were found more than 50 times instead of the expected 1-2 times (FIG. 2A). The nucleotide frequency plots also showed strong bias at most nucleotide positions (FIG. 2B).

Figure 3:
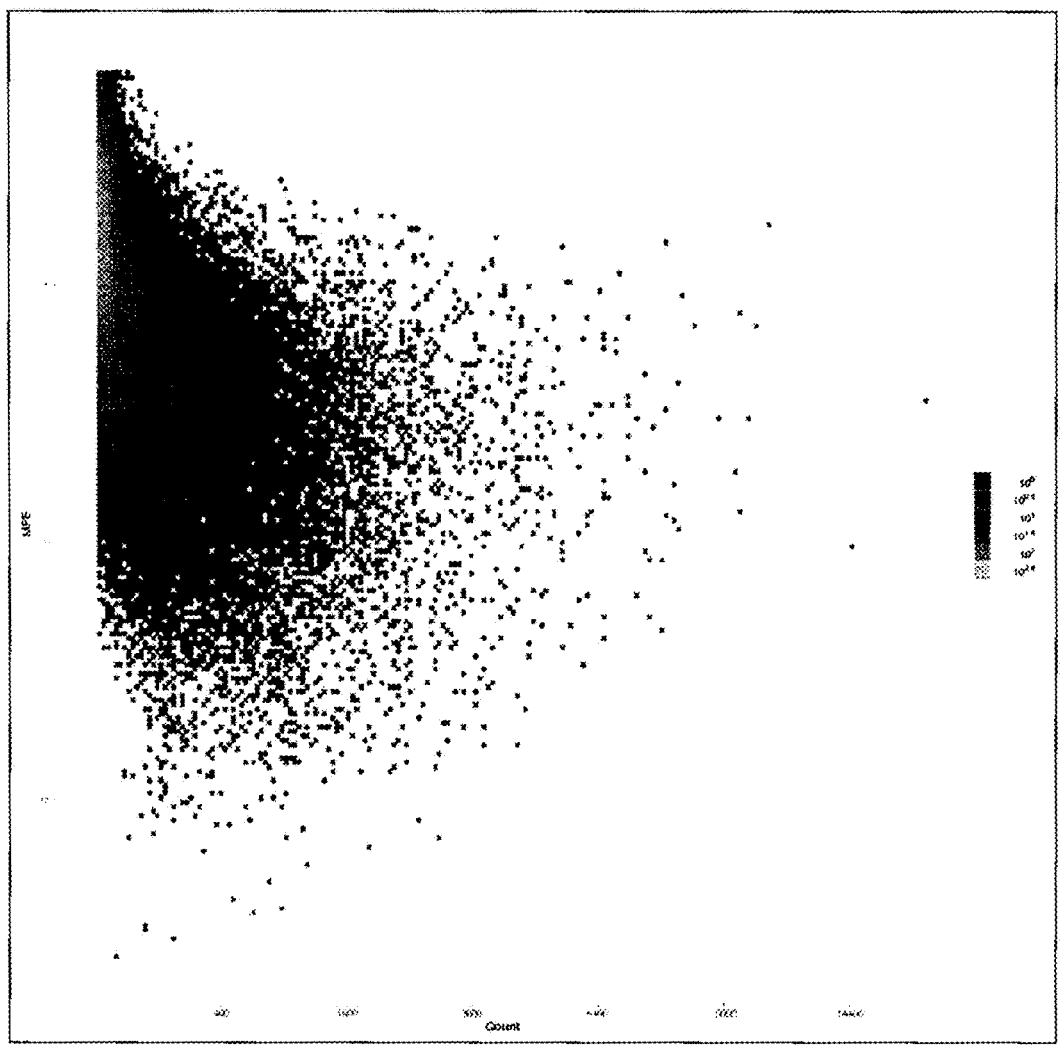
FIG. 3: The secondary structure of each individual N9 synthetic sequence with corresponding Illumina adaptor sequences was folded with RNAfold software. Minimum Free Energy calculated by RNAfold plotted against counts of each sequence. The lower the minimum free energy of the secondary structure with the adaptors the more likely the sequence will be sequenced multiple times (Pearson correlation coefficient equal to 0.67, p-value<10e-15).

The truncated form of T4 RNA ligase 2, which is used to ligate the sRNAs (in our case the N9 and N21 oligonucleotides) to the 3' adaptor, can repair nicks in double stranded RNA (dsRNA) in vitro (Nandakumar and Shuman, 2004). Without wishing to be bound by any particular theory, the present inventors hypothesised that sequences that can form a dsRNA-like structure with the 3' adaptor would be over-represented in the sequenced reads. All sequenced reads were joined to the 3' adaptor sequence and the minimum free energy of the resulting RNA sequences was calculated for each molecule. The abundance of a sequence in the library showed a strong correlation to the value of minimum free energy; the lower the free energy was for a given sequence, the more abundant the sequence was in the library (FIG. 3). Based on this observation the present inventors hypothesised that by adding degenerate nucleotides to the adaptors, the slightly different adaptor molecules will be more likely to form stable secondary structures with different kinds of sRNA sequences. This could allow; 1, the sequencing of sRNAs that are normally not present in libraries generated by the traditional adaptors and 2, the abundance of sequences would reflect better the concentration of the sRNA in the sample. To test this hypothesis four N nucleotides (A, C, G or U) were added to the 5' end of the 3' adaptor and also to the 3' end of the 5' adaptor. These adaptors are referred to as High Definition (HD) adaptors to distinguish them from the Illumina adaptors (which have fixed sequences).

The same N9 and N21 oligonucleotides were used for library generation with the HD adaptors as previously and the libraries were again sequenced on the Illumina GAII platform. Almost twice as many (78% vs. 44%) different sequences were among the reads obtained for the N9 library proving that the HD adaptors were indeed much more sensitive than the Illumina adaptors. The nucleotide frequencies of the reads obtained by the HD adaptors were also much more similar to each other for all the possible different sequences (compare FIG. 1A with 1B and 2B with 2C). Most of the reads for the N21 libraries obtained with the HD adaptors were around the expected 1 to 2 and only a very few reads were present at a higher number (FIG. 2A). These results demonstrate that adding degenerated nucleotides to the end of the adaptors dramatically increase their sensitivity and reduce sequence bias. If severe over-representation of some sequences was observed in biological data it would reduce the average representation of other sequences. Therefore, the potential for sequencing low abundance small RNAs would be reduced and raises the possibility that some small RNAs are 'unclonable' using standard protocol and yet to be identified. The current HD adaptors still show some sequence bias but a systematic survey can establish the optimal position and number of degenerated nucleotides in HD adaptors that would show minimal bias and maximum efficiency using the assay described herein.

Figure 4:
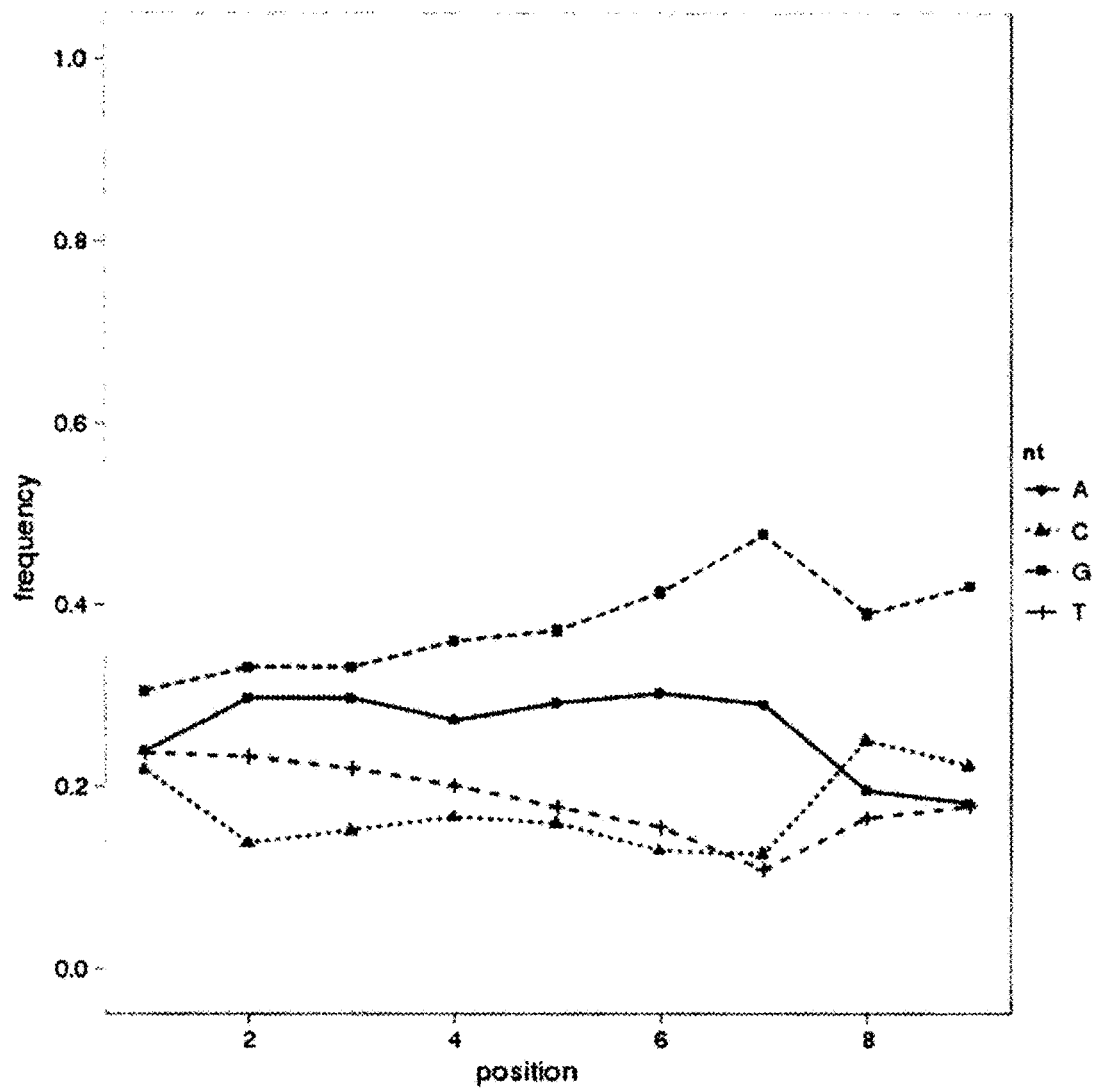
FIG. 4A and FIG. 4B: Nucleotide frequency plots for sequences cloned by HD 3' adaptor GAGATCGTATGC-CGTCTTCTGCTTG (SEQ ID No. 1) (54,023 counts) and ATTGTCGTATGCCGTCTTCTGCTTG (SEQ ID No. 2) (51,928 counts).
Figure 4A:
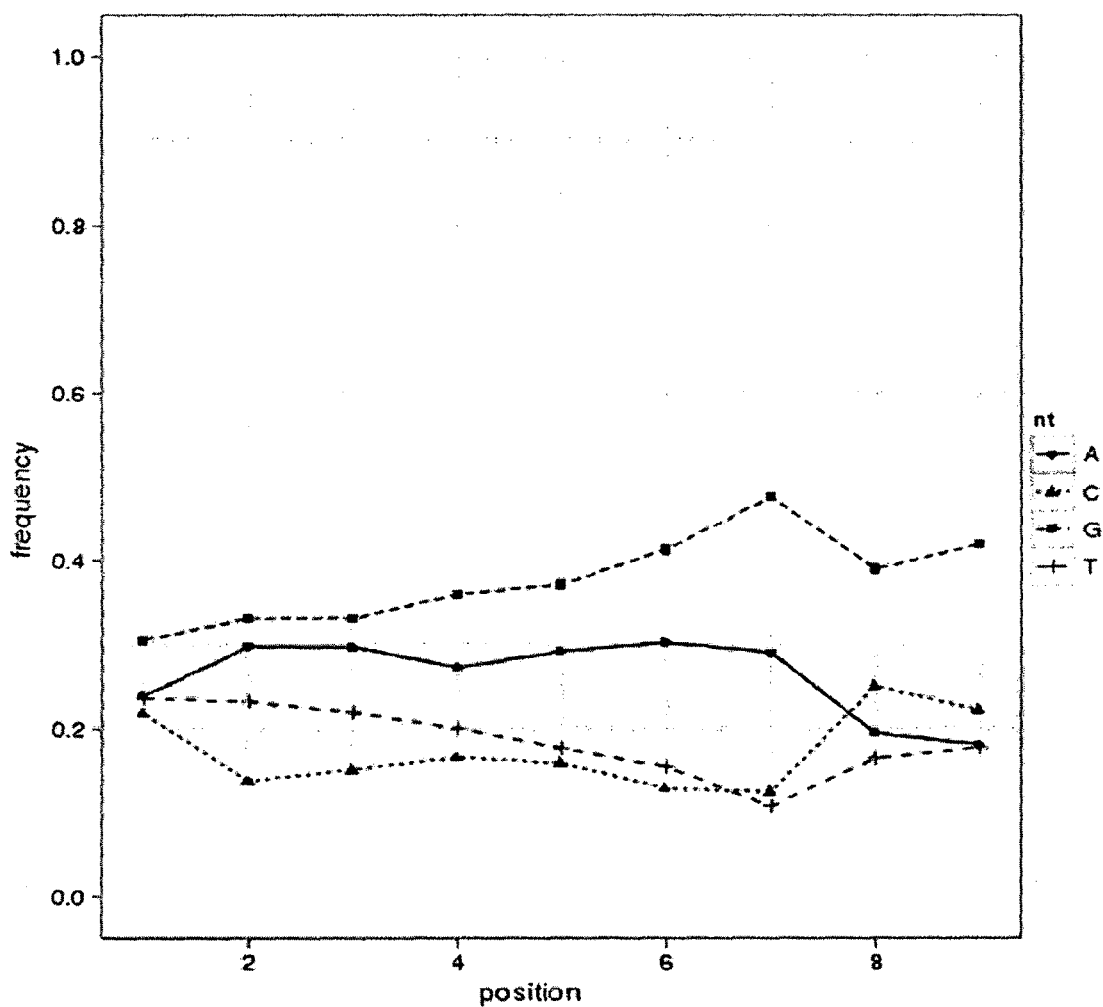
Figure 4B:
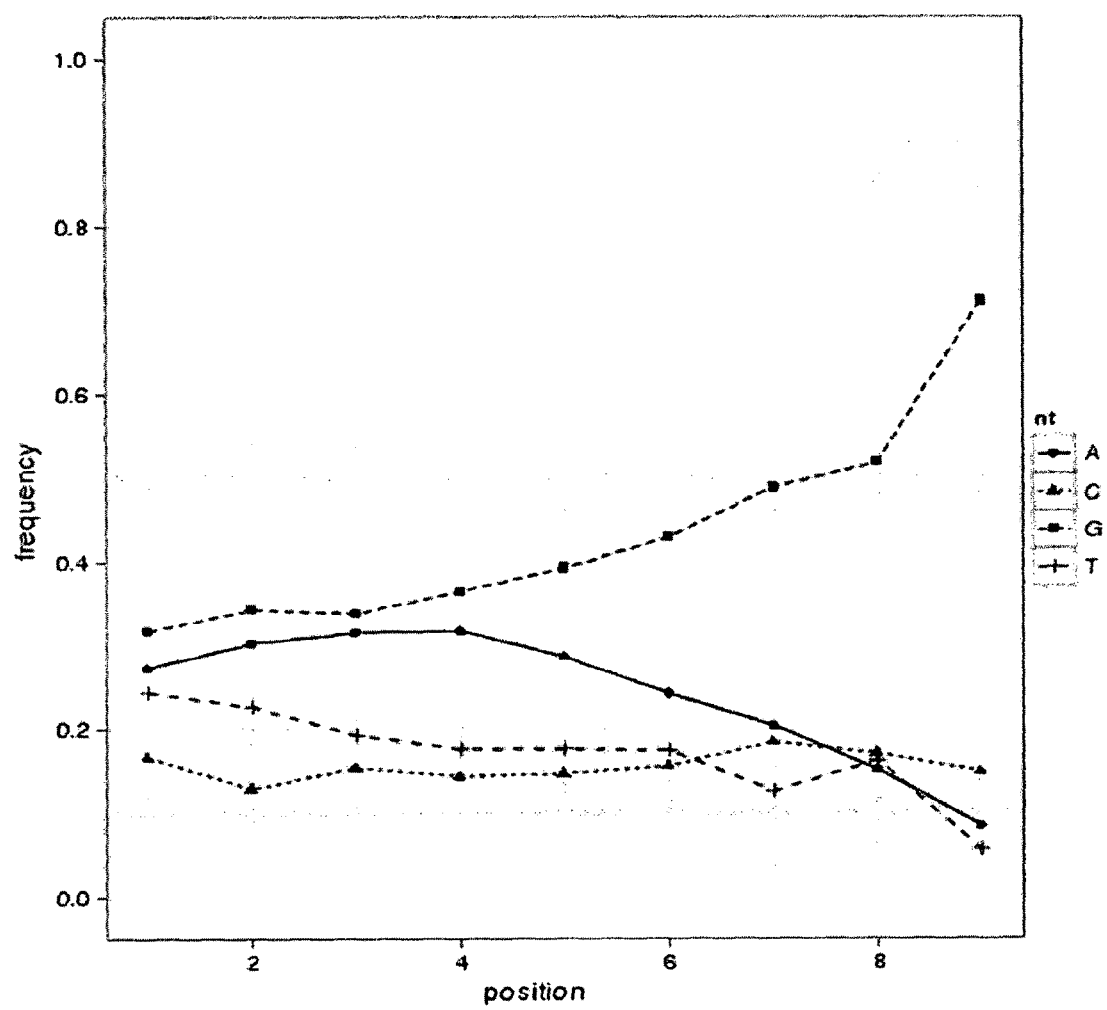

The HD adaptors can also be seen as a complex set of 256 adaptors with 65,536 possible pairs. Individual adaptor pairs had particular preferences for cloning a set of sequences. For example, the 3' HD adaptor with the sequence ATTGTCG-TATGCCGTCTTCTGCTTG (SEQ ID No. 2) had a very strong bias for sequences with Guanine nucleotides at the 3' end when compared with sequences cloned by the 3' adaptor GAGATCGTATGCCGTCTTCTGCTTG (SEQ ID No. 1). 75% of all sequences cloned by ATTGTCGTATGCCGTCT-TCTGCTTG (SEQ ID No. 2) adaptor had a Guanine at position 9 (FIGS. 4A and 4B). This is an important finding and allows the design of unbiased adaptors for multiplexing. Perhaps a more useful application in the future will be the manipulation of bias using adaptors, for example to preferentially sequence low abundance miRNAs associated with disease or to exclude highly abundant sequences that dominate the data.

The HD adaptors were also tested with biological samples. Libraries were generated using either Illumina or HD adaptors from RNA of the MCF7 breast cancer cell line and results were compared to the MCF10a non-cancerous cell line. These experiments were designed to test the efficacy of the HD adaptors for identifying differentially expressed miRNAs and to demonstrate their accurate quantification. These experiments can demonstrate that the use of HD adaptors increases the ability to identify more miRNAs. It was found that a library prepared with HD adaptors identified more than double the distinct sequences that mapped to the genome (Table 1) compared to a library prepared with Illumina adaptors. For example in the MCF7 sample, 23,228 reads per million were distinct using the HD adaptors whereas only 10,903 per million sequences were distinct using the Illumina adaptors.

TABLE 1

Number of distinct and redundant sequences and those mapping to the genome. Normalised data per million reads demonstrate that HD adaptors are more than twice as efficient at cloning small RNAs.

| Cell Line | Distinct Total | Redundant Total | Distinct Mapping | Redundant Mapping | Distinct Mapping per million |
|---|---|---|---|---|---|
| mcf7r1fa | 627509 | 27054847 | 247554 | 22481015 | 11011.69 |
| mcf7r2fa | 542078 | 26769495 | 249639 | 23126674 | 10794.42 |
| mcf7r1va | 705058 | 15459296 | 211847 | 9211267 | 22998.68 |
| mcf7r2va | 759603 | 16391091 | 217605 | 9276366 | 23458 |
| mcf10r1fa | 698069 | 24782969 | 334196 | 19769573 | 16904.56 |
| mcf10r2fa | 466299 | 18008481 | 238092 | 14370373 | 16568.25 |

TABLE 1-continued

Number of distinct and redundant sequences and those mapping to the genome. Normalised data per million reads demonstrate that HD adaptors are more than twice as efficient at cloning small RNAs.

| Cell Line | Distinct Total | Redundant Total | Distinct Mapping | Redundant Mapping | Distinct Mapping per million |
|---|---|---|---|---|---|
| mcf10r1va | 989636 | 12728537 | 257233 | 6545624 | 39298.47 |
| mcf10r2va | 1002778 | 12330132 | 243861 | 6134363 | 39753.27 |

Figure 5:
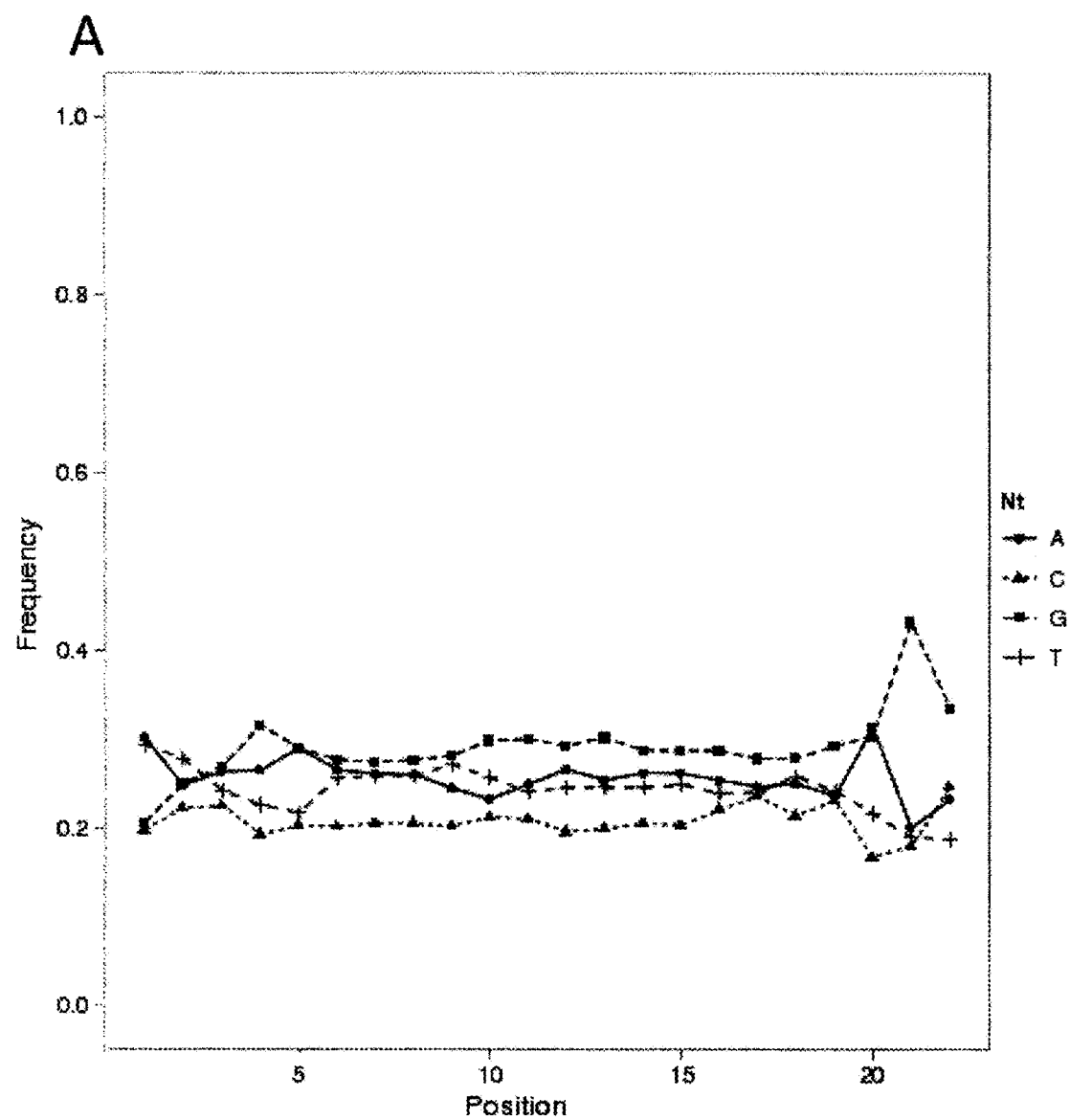
FIG. 5: Analysis of sequence data from biological samples that map to the genome. Nucleotide frequency plots showing proportion of each nucleotide at each position in the 22 nt sequences. A and B are MCF7 samples and C and D are the MCF10a samples. E is a whole mouse sample. Illumina adaptors show bias for sequences with the nucleotide Guanine at the two penultimate 3' nucleotides (positions 20 and 21) (A and C), which is similar to the bias observed in the synthetic samples. HD adaptors have significantly reduced bias and lines are close to the theoretical optimum of 0.25 frequency (B and D). The mouse sample cloned with the HD adaptors has similar low bias as the MCF7 and MCF10a HD adaptor samples.
Figure 5:
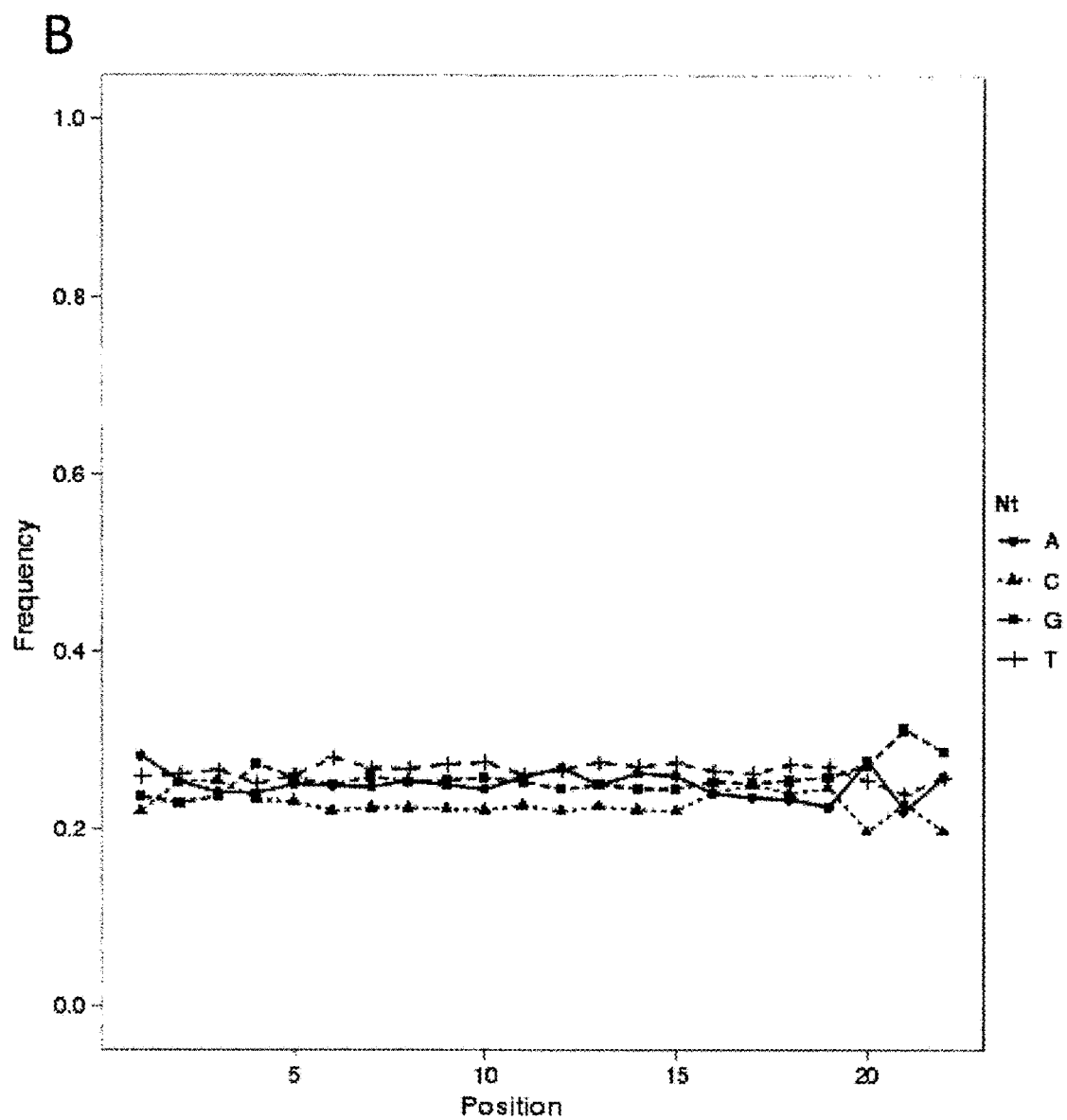
Figure 5:
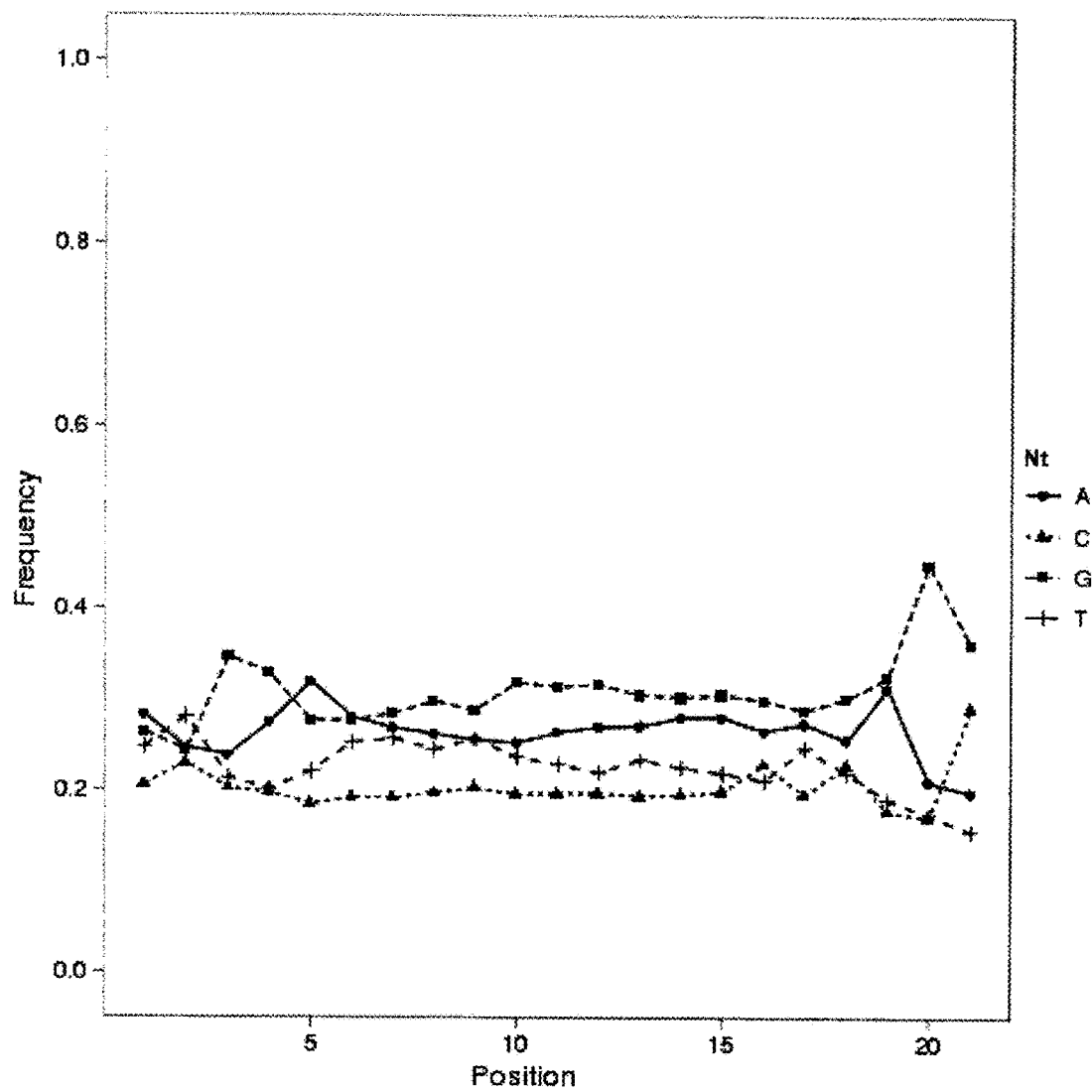
Figure 5:
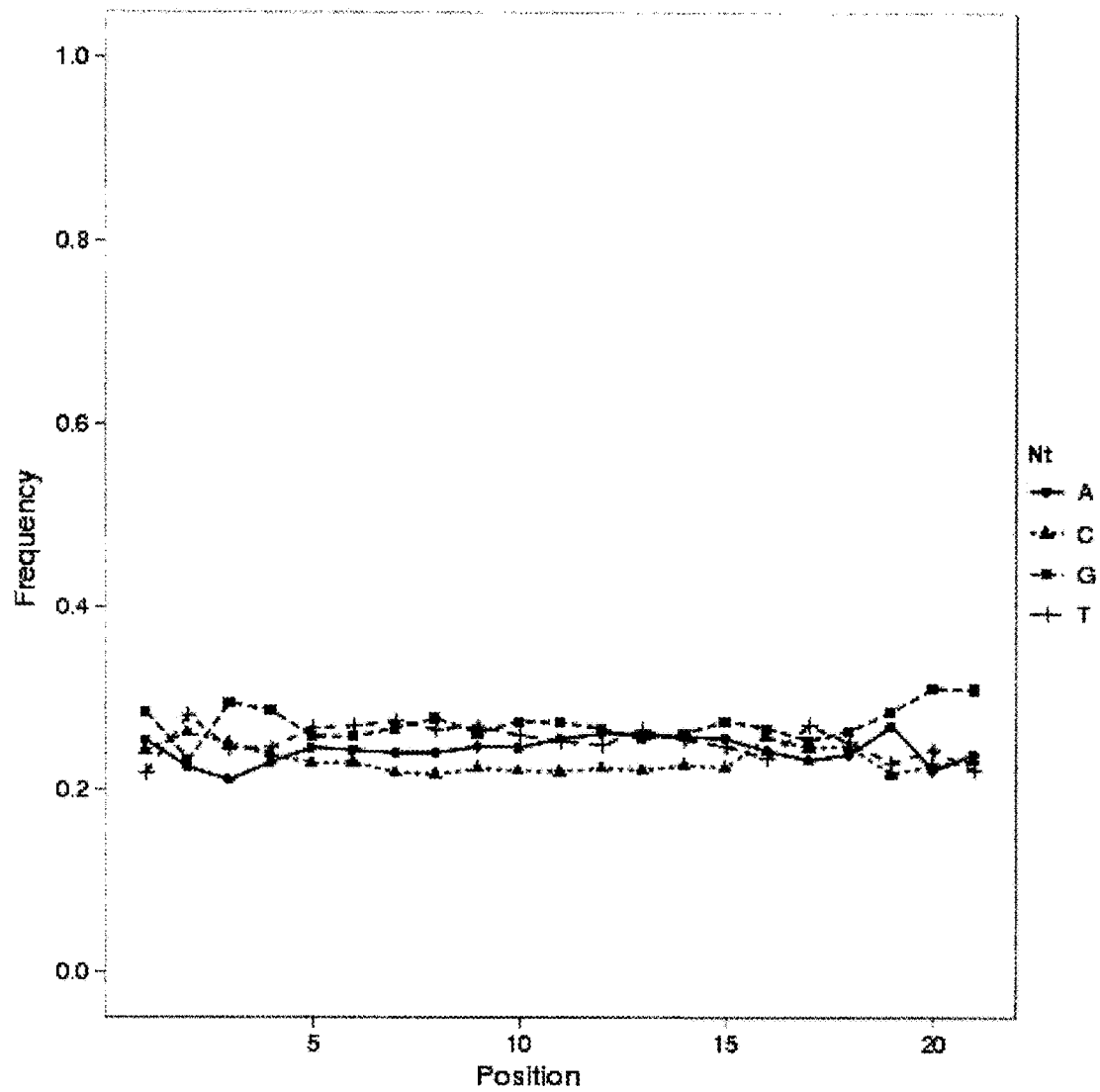
Figure 5:
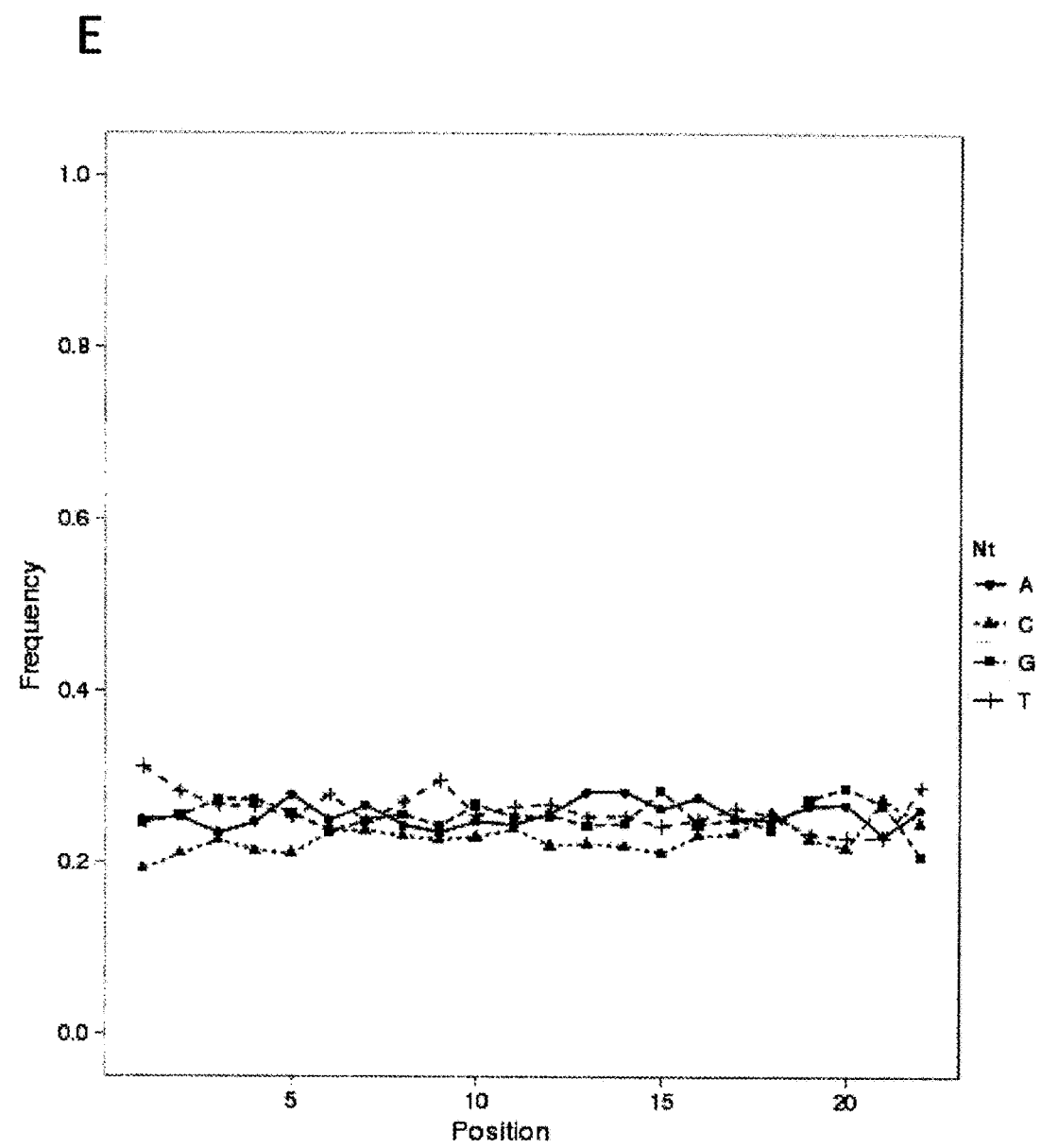

The increase in complexity of the sequenced reads causes a concomitant reduction in sequence bias for the HD data set. This can be observed in the nucleotide frequency plots (FIG. 5; compare A with B and C with D). The sequence bias in libraries generated from cell lines is expected to display considerable bias because the microRNA repertoire is limited. Libraries generated from many tissue types would be expected to capture a more diverse set of small RNAs and have further reduced bias. Libraries were generated from whole mice (postnatal-P3 C57). As expected many more sequences that mapped to the mouse genome were distinct (47,674 mouse vs. 23,228 MCF7 vs. 39,525 MCF10a per million) and in this data set sequence bias is further reduced compared to MCF7 and MCF10a samples (FIG. 5E).

Figure 6:
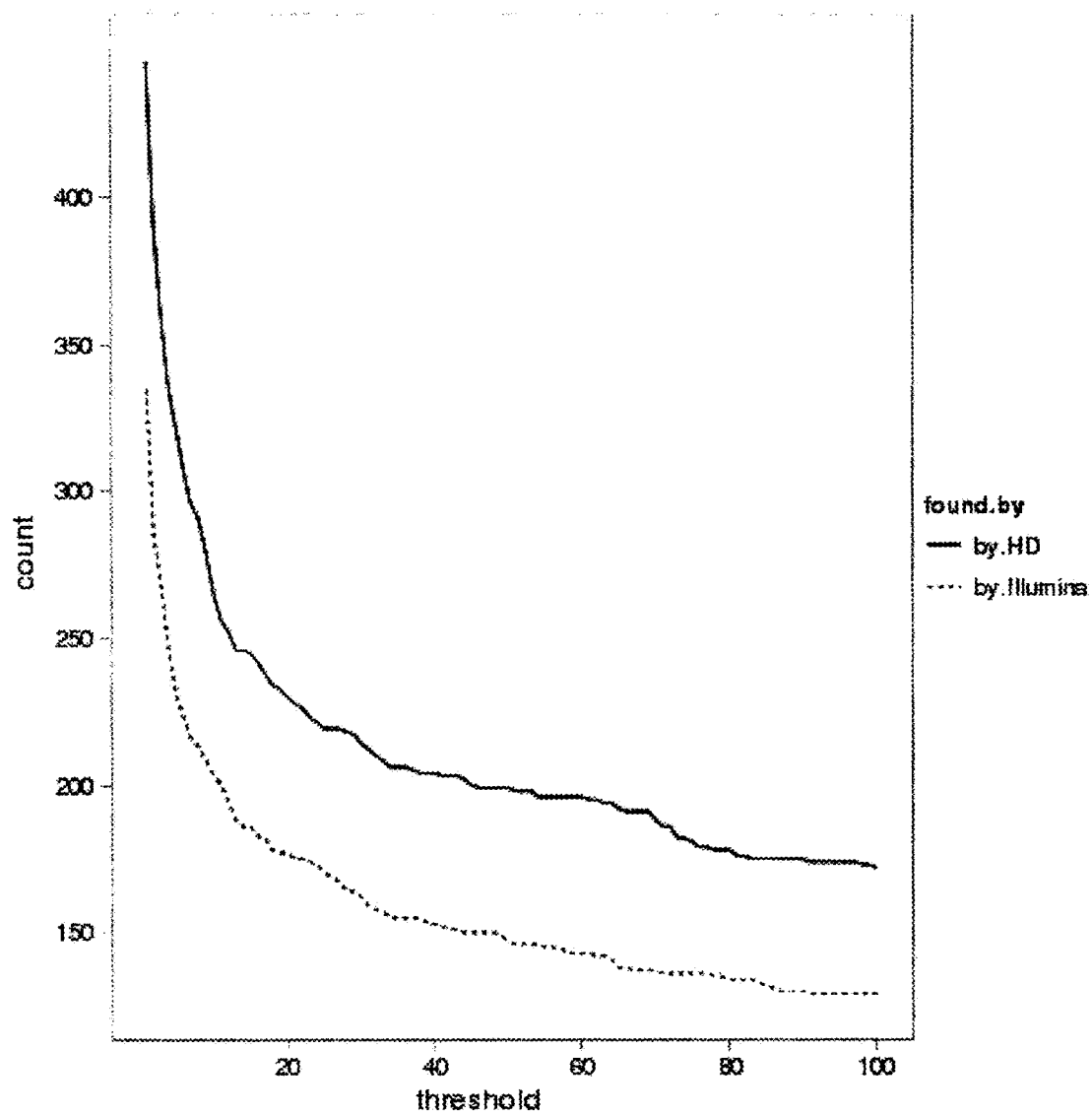
FIG. 6: Number of known miRNAs identified with increasing threshold in MCF7 samples cloned with Illumina adaptors and HD adaptors. Sequences with read numbers below the threshold are excluded from the count. HD adaptors identify more miRNAs at all thresholds.
Figure 7A:
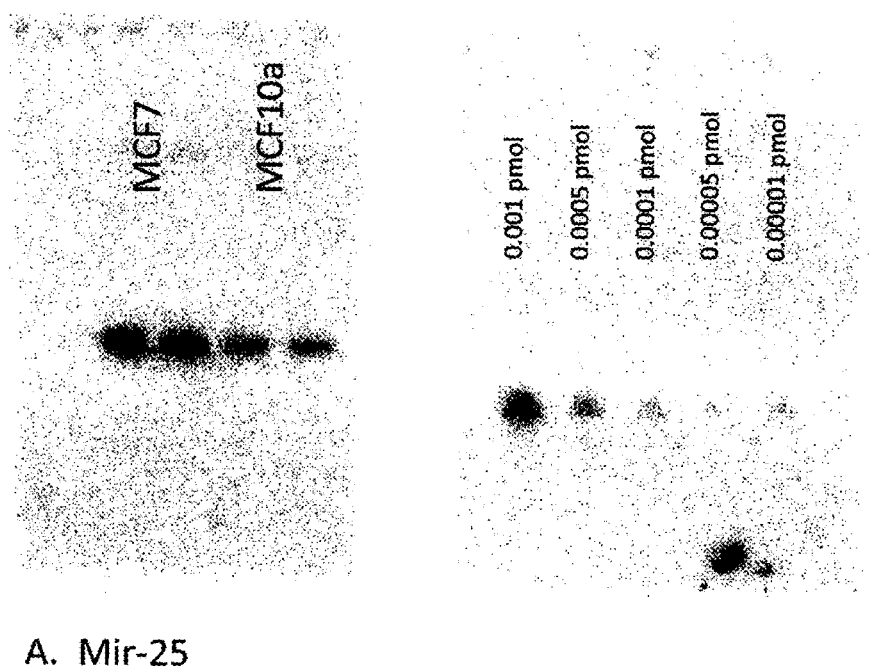
FIG. 7: Absolute quantification by Northern blot analysis. A and B. Spot densitometry was used to compare band intensity of signal from biological samples MCF7 and MCF10a with a standard concentration curve that used an oligonucleotide with the identical sequence to the miRNA. C. Number of reads for hsa-mir-103 and hsa-mir-25 using Illumina or HD adaptors. D. Absolute quantification shows that hsa-mir25 is ~10 fold more abundant than hsa-mir-103. This is similar to quantification by HD adaptors.
Figure 7B:
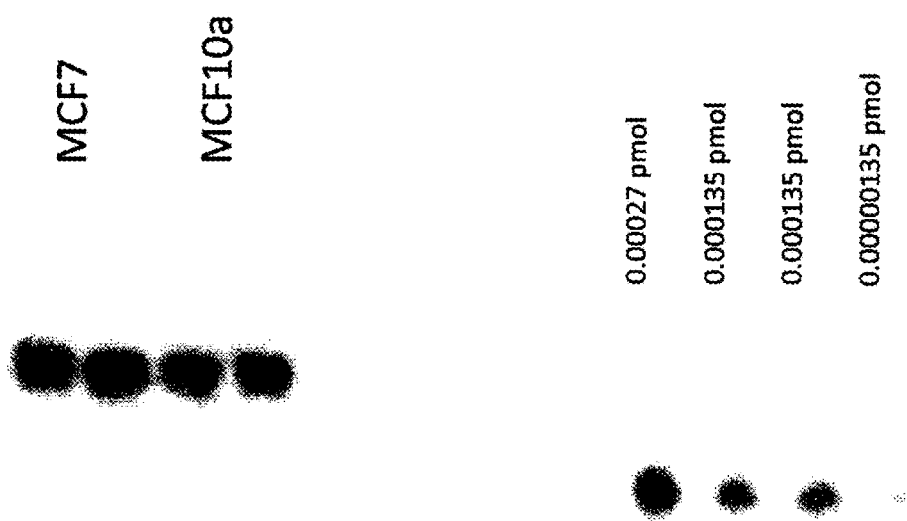
Figure 7C:
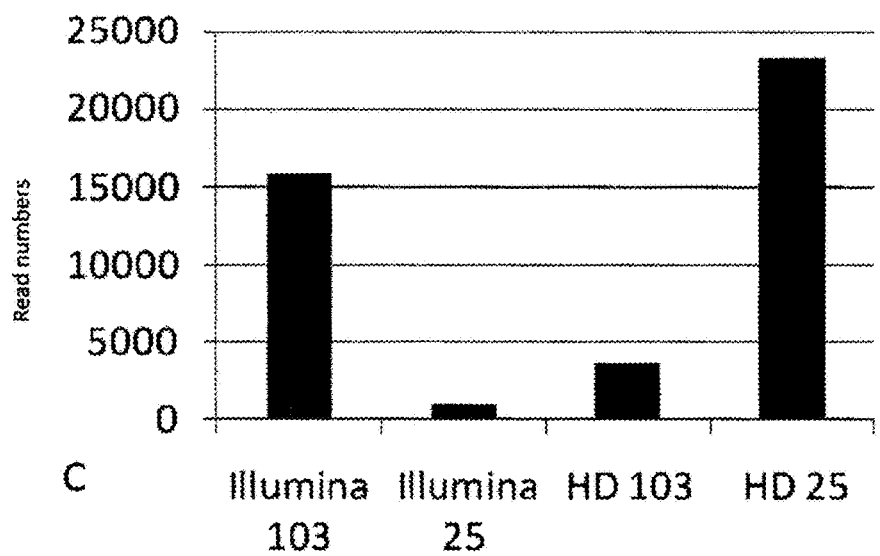
Figure 7D:
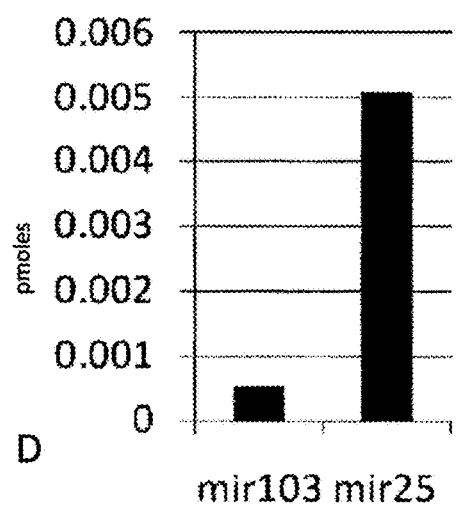

It is often valuable to identify which miRNAs are expressed in a dataset. To demonstrate that HD adaptors produce data with more identifiable miRNAs, the inventors searched for known miRNAs in the data set. FIG. 6 shows the number of sequences that achieve a threshold number of reads. At a threshold level of 5 reads per million, only ~250 known miRNAs are identified from Illumina adaptors but HD adaptors identify ~350. As this threshold increases fewer miRNAs are identified in both Illumina and HD adaptor datasets. However, more known miRNAs were identified using the HD adaptors than the Illumina adaptors at any particular threshold.

The absolute quantification of some miRNAs was more similar to the read numbers generated by the HD adaptors (FIG. 7). For example, using northern analysis it was found that the absolute quantification of mir25 (0.508 nM) was 9.5 fold greater than mir-103 (0.0537 nM). However, the data set generated with the Illumina adaptors suggested the opposite relationship; that the mir-103 sequence (15,877 reads) was 15 fold more prevalent than the mir-25 sequence (1035 reads). The HD adaptor data set was able to correctly predict the relative quantities of these two miRNAs; mir-25 (23,269 reads) had 6.4 fold greater reads than mir-103 (3610 reads).

Figure 11A:
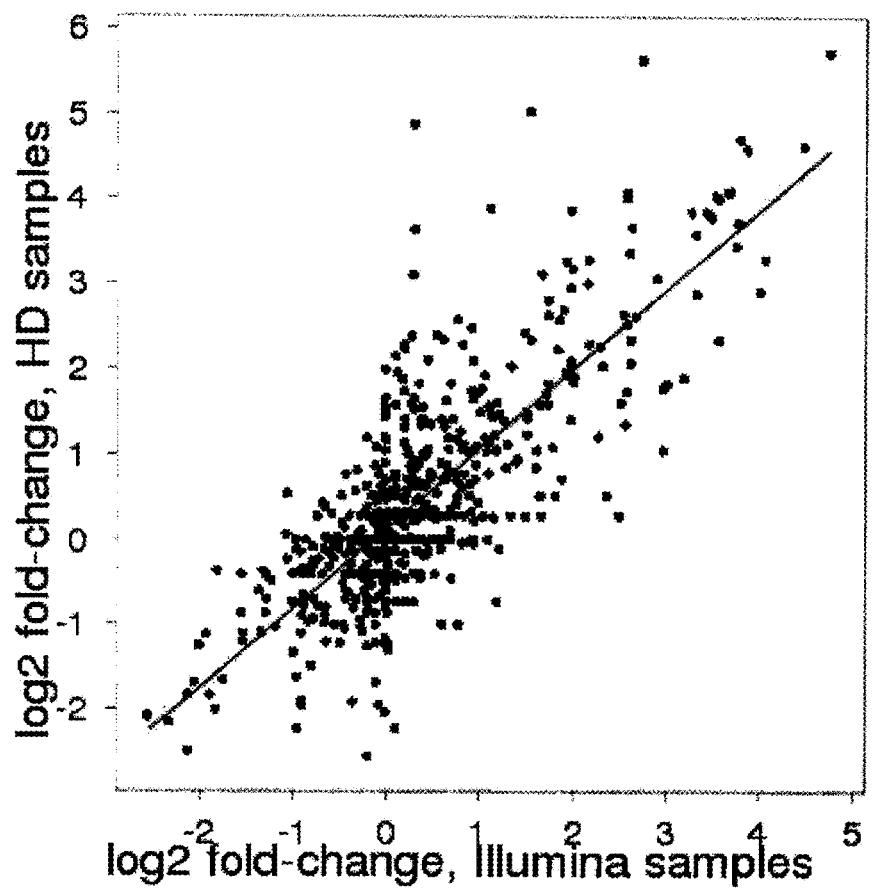
FIG. 11. cDNA library preparation protocols distort miRNA research. (a) Comparison of change in miRNA level between wild-type and Dicer KO DLD cells obtained in Illumina (x axis) and HD samples (y axis). R2=0.62 (b) Number of known miRNAs found in DLD cells at different thresholds using Illumina or HD adapters. Regardless of chosen threshold, HD adapters identify more miRNAs. (c) Absolute quantification of eight known miRNAs (let-7i, miR-10a, miR-19b, miR-21, miR-25, miR-29b, miR-93, miR-375) obtained by Northern blot compared with number of times these miRNAs were sequenced using Illumina or HD adapters in DLD cell line. Data obtained with HD adapters correlates better with absolute quantifications (R2=0.70) than Illumina data (R2=0.12). Number of PubMed citations and number of reads per experiment (data obtained from miRbase v17) of human miRNAs. miRNAs with higher number of reads tend to be more extensively studied.

The inventors next tested the HD adapters on the DLD-1 colon cancer cell line and DLD-1 Dicer exon5 partial KO mutant cell line. Given that the biases are expected to be sequence specific, the same sequences in different samples will be subject to similar biases. Fold change expression analyses are therefore largely unaffected by these biases. It was confirmed that the fold change of miRNA expression between DLD-1 WT and DLD-1 Dicer KO were similar in libraries using HD and Illumina adapters (FIG. 11a). Therefore both HD and Illumina adapters are valuable for identifying differentially expressed sRNAs.

Figure 11B:
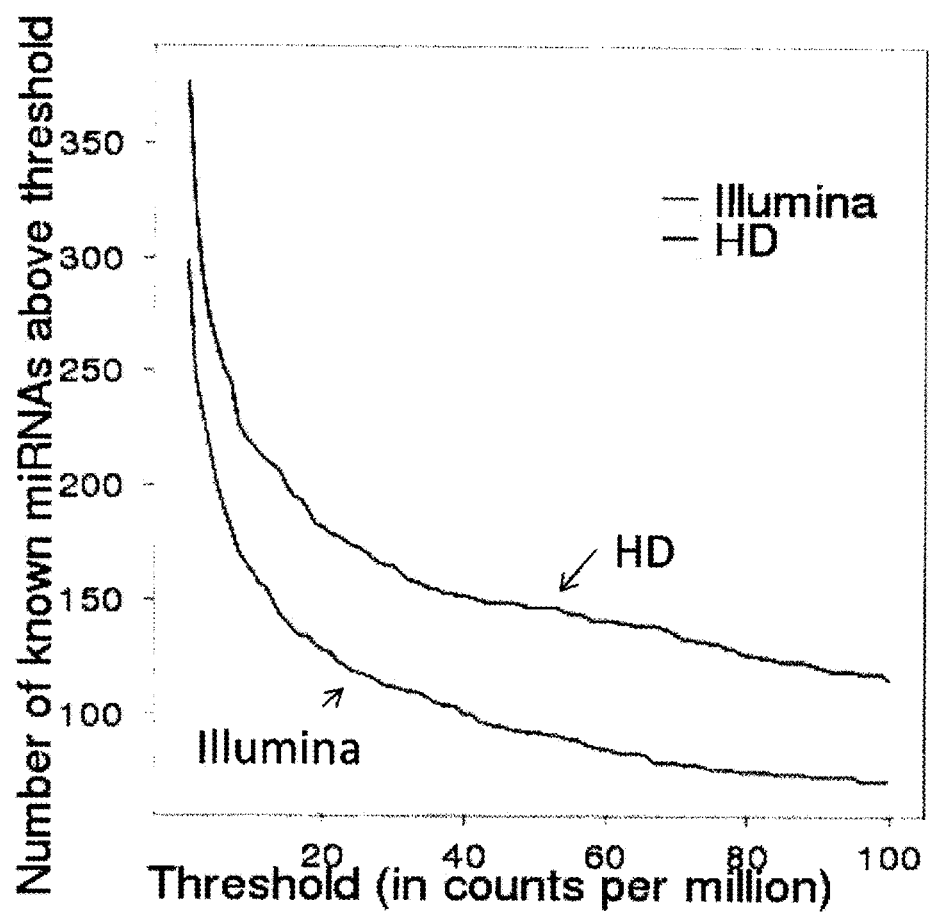
Figure 11C:
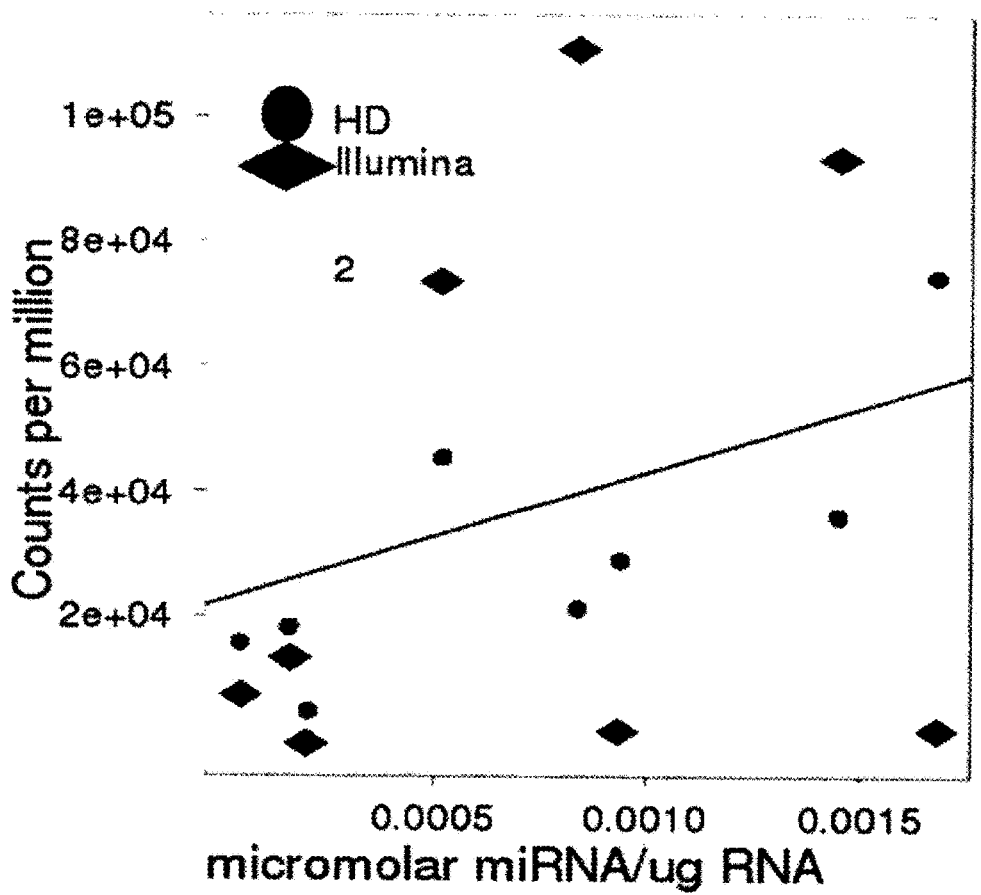
Figure 12:
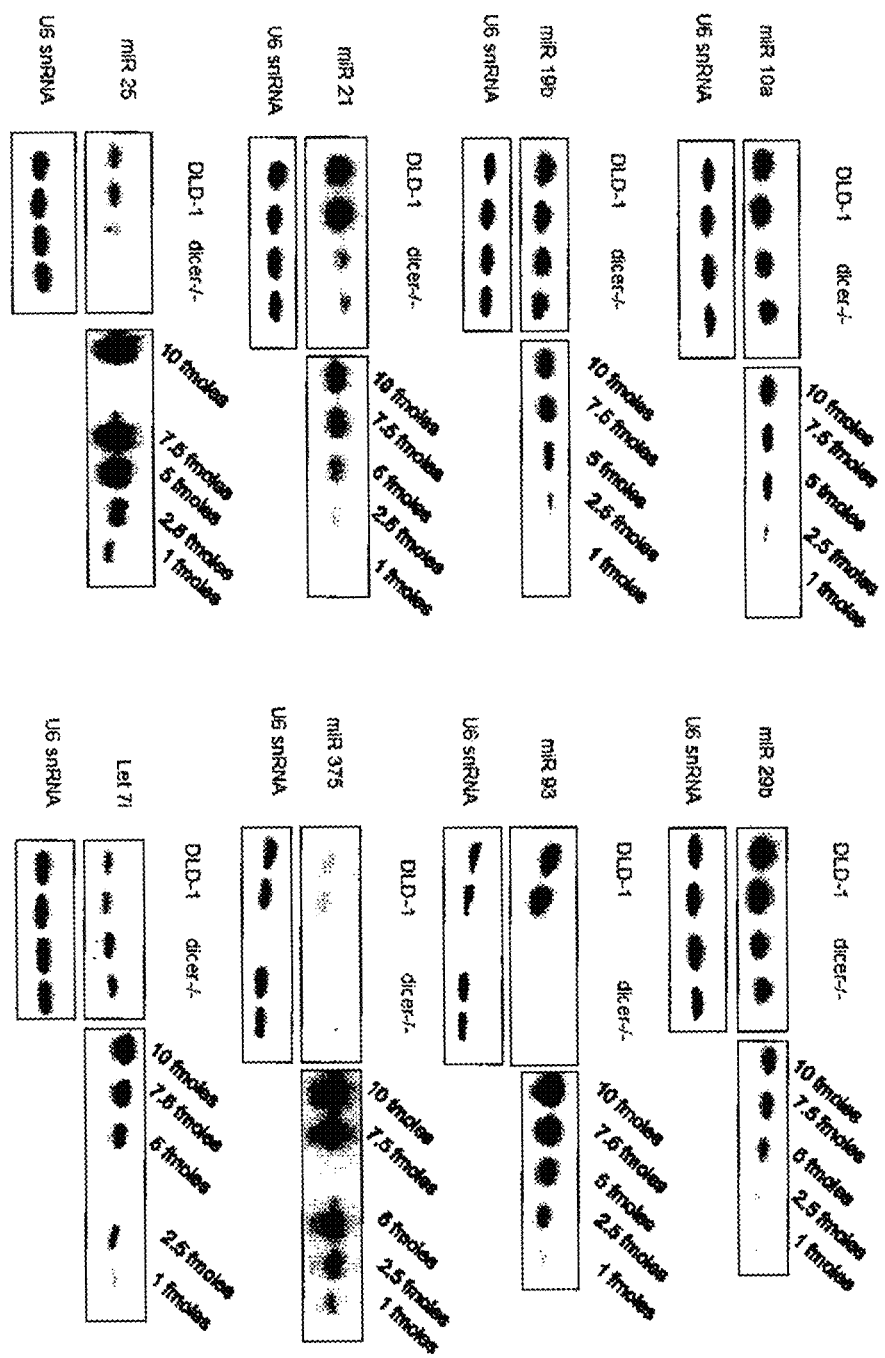
FIG. 12. Quantification of known microRNAs in DLD-1 cells (epithelial adenocarcinoma cells), both wild-type and dicer−/−. Total RNA (10 μg) was analysed via Northern blot and microRNA experimental samples were quantified using a serial dilution of synthetic oligonucleotide sequences corresponding with the miR of interest. The small nuclear RNA U6 was used as a loading control, and this U6 image has been duplicated where different microRNAs were analysed on the same membrane (miRs 10a & 29b and miRs 25 & Let 7i).

The accurate quantification of sRNAs is crucial because researchers focus on miRNAs with high read numbers. The inventors found that miRNAs with high read counts in miRBase were significantly more likely to be cited by the research community. (R2=0.25, p=10-15). This is not surprising because usually miRNAs that are highly expressed (i.e. have high read numbers) and show the strongest differential expression compared to another sample (control or another treatment or another tissue, etc.) are selected for in-depth, functional analysis. The miRNAs were ranked based on their normalised read number in DLD-1 cells using either HD or Illumina adapters. The most abundant miRNA in the HD adapter-generated libraries was miR-29b with more than 150,000 reads per million reads, which is almost twice as high as the next miRNA. Therefore it would be reasonable to choose miR-29b for further analysis if one was interested in the role of miRNAs in colon cancer biology. However, using the Illumina adapters, miR-29b was only the 29th on the ranked list with 3,336 normalised reads, while the top four miRNAs had more than 100,000 normalised reads in that library. It is clear that miR-29b would not be chosen for further analysis based on the Illumina sequencing result. Furthermore, only five of the top ten most sequenced miRNAs using the HD adapters were also in the top ten most sequenced miRNAs using Illumina adapters. Therefore, the prioritisation of miRNAs for in-depth analysis could be highly dependent on the adapters used, at least for some samples. Quantitative Northern blot analysis was used to demonstrate that libraries made with HD adapters accurately reflected cellular abundance of the sRNAs but libraries made with Illumina adapters did not (FIG. 11c, FIG. 12). Not all miRNAs show such a dramatic difference in the two ranked lists (e.g. miR-93 and miR-10a were ranked second and third on the HD adapter list, and fourth and second on the Illumina adapter list, respectively) but the example of miR-29b illustrates that potentially many miRNAs were not chosen for functional analysis in previous studies. Next the inventors investigated the sequence coverage of HD adapters. It was found that the HD protocol identified more than double the distinct sequences that mapped to the genome compared to a library prepared with Illumina adapters. HD adapters also captured approximately 25% more known miRNAs at any particular count threshold compared to Illumina adapters (FIG. 11b). HD adapters were also able to capture previously unidentified miRNAs. The miRCat algorithm (Moxon et al 2008) was used to identify 32 candidate miRNAs using HD or Illumina data. In addition to identifying 309 known miRNAs in this cell line the HD adapters were able to capture 26 new miRNAs. Five of these were also sequenced by the Illumina adapters, but there were only three new miRNAs, which were only captured by the Illumina adapters. The normalised read number of these 29 new miRNAs was at least 1.4 fold lower in the Dicer KO DLD-1 cell line, supporting that they are generated by Dicer. In addition, the inventors searched deep sequencing data in miRBase and found reads matching the putative miRNA* sequences for all new miRNA genes. Seventeen of these new miRNAs (13 captured only by the HD adapters) could not have been found previously as they are not included in any of the raw sequences deposited in miRBase from more than 100 different deep sequencing experiments. It is therefore reasonable to suggest that new miRNAs will be identified in other tissues, especially in brain tissue, which shows the most diverse miRNA population.

Another consequence of the ligation bias is the potential mis-annotation of the two strands of a miRNA duplex. The active 'mature miRNA' is usually determined by higher read numbers compared to the 'star' sequence and these frequencies can be estimated by the ratio of counts of the two strands. However, these estimates are also prone to be distorted by ligation biases potentially leading to incorrect annotation of mature and star. The count ratios were compared for all annotated pairs of miRNAs derived from the same precursor expressed at a moderate to high level (>10 reads per million), using the DLD-1 Illumina and HD data sets. Although the correlation between the ratios obtained with the two protocols was relatively strong (R2=0.69, data not shown), the inventors found 15 pairs out of the analysed 122 miRNA/miRNA* pairs for which the miRNA strand with a higher read number was different in the data obtained with Illumina and HD adapters.

The HD adaptors still generated some sequence bias. Sequences that were predicted by RNAfold (Hofacker 2003) to have strong secondary structures with the adaptor sequences were preferentially sequenced. It was not possible to alter this core sequence, but removing the effects of this core sequence should significantly reduce sequencing bias. This could be done in two ways. An adaptor with a degenerate sequence and custom sequence could be ligated to the small RNA followed by PCR with an oligo to incorporate the Illumina adaptor sequence. Alternatively the core adaptor sequence could be blocked from forming secondary structures by using a complementary oligonucleotide, for example:

```
5' ADAPTOR(r = RNA)
5' GTTCAGAGTTCTACAGTCCGACGATCrNrNrNrN 3'    (SEQ ID No. 3)
   ||||||||||||||||||||||||||
3' CAAGTCTCAAGATGTCAGGCTGCTAG 5'             (SEQ ID No. 4)

3' ADAPTOR(r = RNA)
5' rNrNrNrNATCTCGTATGCCGTCTTCTGCTTG 3'       (SEQ ID No. 5)
           ||||||||||||||||||||||||
3'         TAGAGCATACGGCAGAAGACGAAC 5'       (SEQ ID No. 6)
```

Figure 8:
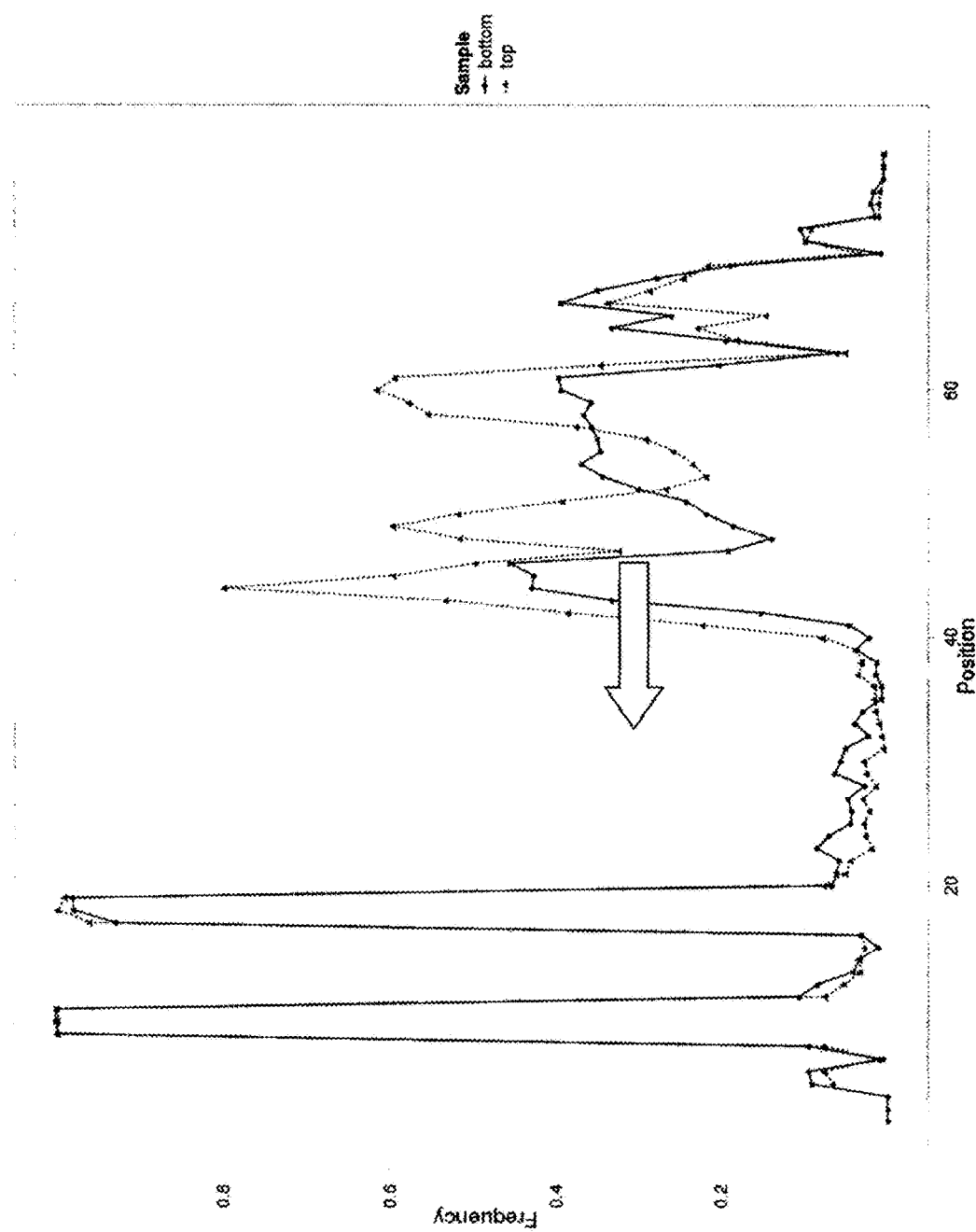
FIG. 8: Frequency of predicted nucleotide base-pairing per position using DNA folding parameters, temperature equal to 50° C. A. N9 artificial ligation product has increased nucleotide base-pairing at the 3' end of the reverse primer (arrow). Solid line and circles represent a set of sequences with the top 5,000 number of reads. As a comparison dashed lines and triangles represent set of sequences with the bottom 5000 number of reads. B. N21 artificial ligation product also has increased nucleotide base pairing at the 3' end of the reverse primer. Solid line and circles represent a set of sequences with the top 10,000 number of reads. As a comparison dashed lines and triangles represent a set of randomly generated sequences.
Figure 8:
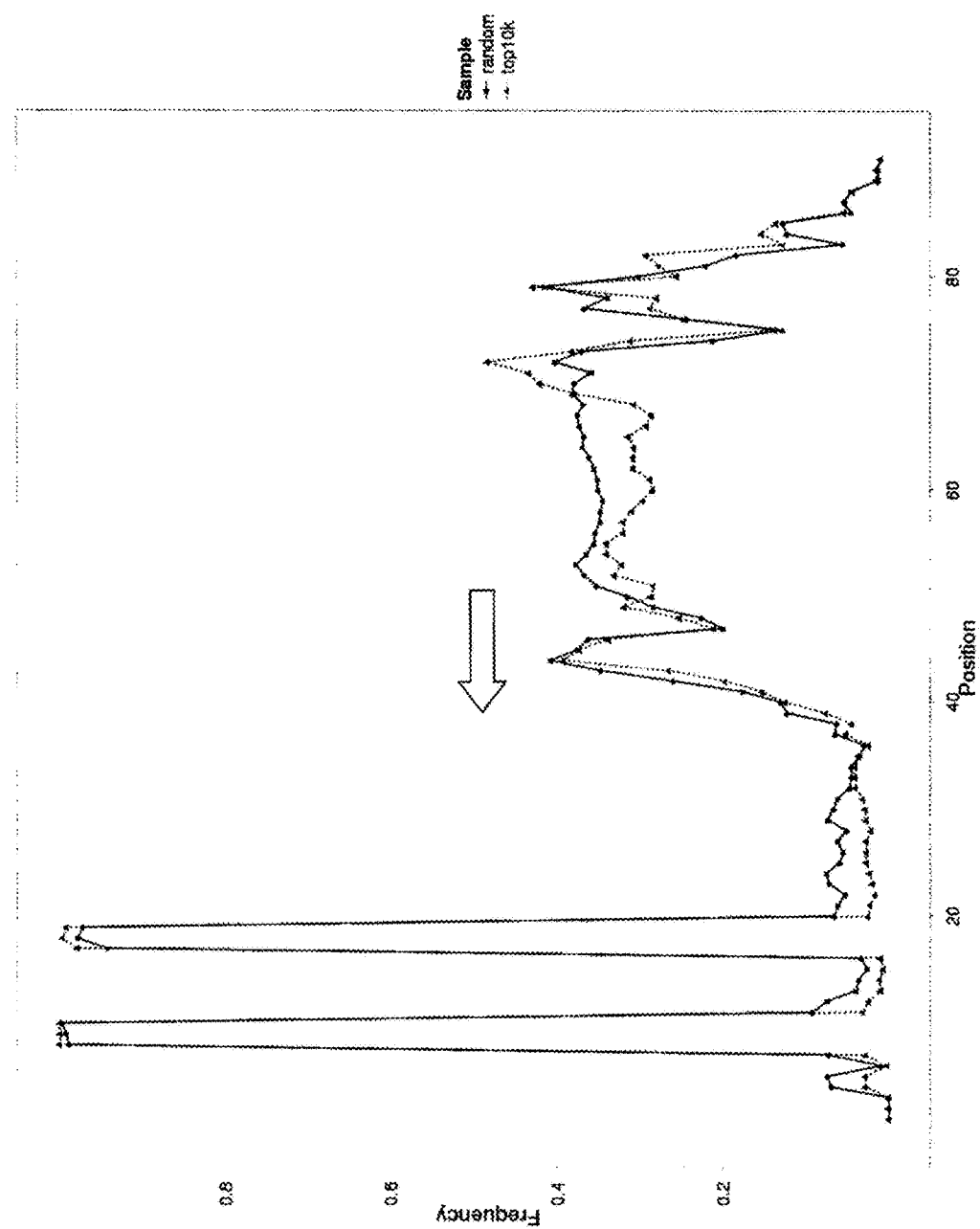

PCR bias is also a contributing factor when generating a small RNA library. Using a degenerate DNA sequence flanked by the Illumina PCR priming sites, the present inventors have also shown that PCR bias was minimal for the N9 sample but was higher for the longer N21 sample (FIGS. 1C and 2D). This suggests that as the cloned sequence gets longer PCR bias is increased. Sequences that have high G/A content are particularly favoured during PCR and sequencing. The inventors also found a relationship between the secondary structure of the PCR product and the read counts (FIG. 8). For the N9 sample the correlation between the number of reads for each sequence and the respective minimum free energies, approximately equal to 0.1, was found to be statistically significant (t-test p-value<$10^{-15}$).

RNA Seq

This method is an alternative to microarray analysis for transcriptome analysis. It has the advantage of identifying previously unknown genes and is predicted to supersede microarrays. Sequence bias has been identified for small genes and genes that are AT rich (Oshlack and Wakefield 2009), and by random hexamer priming library generation method (Hansen, Brenner et al. 2010). HD adaptors could reduce bias for some methods of generating libraries. HD adaptors could be used in protocols where the mRNA is sheared and then adaptors ligated. Reverse transcription then follows after ligation. Sequencing coverage when using HD adaptors could be more even across genes of interest.

Genome Sequencing

Genomic libraries are generated from sheared double stranded DNA. The sheared DNA is made blunt ended and then 'A' overhangs are generated. The adaptors have 'T' overhangs and are ligated to the DNA with DNA ligase. Illumina and Solid sequencing technologies are biased against AT rich regions (Dohm, Lottaz et al. 2008; Harismendy, Ng et al. 2009) but do not have significant bias at sequence ends (Hansen, Brenner et al. 2010). HD adaptors may help to reduce bias if DNA ligase has any sequence preference. Furthermore, degenerate nucleotides may help to reduce the AT composition of some sequences which could result in increase reads. It may also be desirable to increase the nucleotide degeneracy at the ligation sites. Rather than just using T overhangs G/T overhangs on the adaptors could be used in conjunction C/A overhangs on the inserts.

QPCR

QPCR is particularly challenging for quantifying small RNAs for at least the following reasons:

(i) mature miRNA are short (~22 nucleotides; nts);
(ii) miRNAs are heterogeneous in their GC content, which results in a relatively large interval of melting temperature ($T_m$) of nucleic acid duplexes for the population of miRNAs;
(iii) mature miRNAs lack a common sequence feature that would facilitate their selective purification [e.g., poly (A)];
(iv) the target sequence is present in the primary transcript (pri-miRNA) and the precursor (pre-miRNA), in addition to the mature miRNA;
(v) miRNAs within the same family may differ by a single nucleotide (e.g., Let-7 family).

Strong biases can be caused by the different library preparations (Linsen, de Wit et al. 2009; Benes and Castoldi 2010). Using modified HD adaptors may help reduce these biases. A suggested HD adaptor for QPCR may have a fixed region (so that the PCR primer $T_m$ can be adjusted) followed by 20 degenerate nucleotides and a 3' fixed sequence for Reverse transcription and PCR.

For example:

```
                                                    (SEQ ID No. 7)
5' CAAANNNNNNNNNNNNNNNNNNNNNNFIXEDSEQUENCE 3'
```

The fixed sequence could blocked from annealing by a complementary oligo to further reduce bias.

Methods

1. Isolate small RNAs using kit such as Mirvana small RNA isolation kit (Ambion).
2. Mix the following:
   0.5 µL 3' high definition adenylated adaptor (5 µM)
   2.5 µL small RNA enriched RNA
3. Heat sample at 70° C. for 2 minutes, then immediately place sample on ice.
4. Add the following:
   0.5 µL truncated ligase buffer (NEB)
   0.4 µL MgCl$_2$ 100 mM
   0.75 µL Truncated ligase (NEB)
   0.25 µL RnaseOUT (Invitrogen)
5. Incubate sample at 22° C. for 1-2 hrs.

6. Heat 5' high definition adaptor at 70° C. for 2 minutes, then place on ice.
7. Add the following:
0.5 μL ATP (10 mM)
0.5 μL 5' high definition adaptor
0.5 μL ssRNA ligase (NEB)
8. Incubate sample for 1-2 hrs at 20° C.
9. Add the following to ligated RNA (6.9 μL)
1.5 μL diluted RT primer (5 μM)
10. Incubate at 70° C. for 2 mins.
11. Add the following:
3 μL 1st strand Reverse transcriptase buffer (Invitrogen)
0.75 μL dNTPs (10 mM)
1.5 μL DTT (Invitrogen)
0.75 μL RNAaseOUT (Invitrogen)
12. Incubate at 48° C. for 3 minutes.
13. Add 1.5 μL Superscript II (Invitrogen).
14. Incubate at 44° C. for 1 hr.
15. Perform PCR. Add the following:
12.9 μL Water
4 μL 5× Buffer (Finnzymes)
0.2 μL GX1 primer (50 μM)
0.2 μL GX2 primer (50 μM)
0.5 μL dNTPs (10 mM)
0.2 μL Phusion Polymerase (Finnzyme)
2 μL Reverse Transcription reaction
Perform PCR cycles
98° C. 30 s seconds
then 8-13 cycles
98° C. 10 seconds
60° C. 30 seconds
72° C. 15 seconds
then 72° C. for 10 mins
16. Run sample on Polyacrylamide Gel (8%) at 150V for 1 hr.
17. Isolate gel fragment corresponding to ~100 bp.
Adaptor sequences (r=RNA; App=Adenosine diphosphate)
Illumina adaptors v1.5 'Fixed':

(SEQ ID No. 8)
5'rGrTrTrCrArGrArGrTrTrCrTrArCrArGrTrCrCrGrArCrGrArTrC 3'

(SEQ ID No. 9)
5'ApprATCTCGTATGCCGTCTTCTGCTTG 3'

'High Definition' adaptors:

(SEQ ID No. 10)
5'GTTCAGAGTTCTACAGTCCGACGATCNrNrNrN 3'

(SEQ ID No. 11)
5'ApprNrNrNNTCGTATGCCGTCTTCTGCTTG 3'

DNA Polymerase and RNA Ligase Function Investigation

The method of the invention was also used as an effective way to investigate the function of nucleic acid modifying enzymes such as DNA polymerase and RNA ligases.

Assuming that the degenerate library presented to the enzyme is equimolar, if the efficiency of the reaction catalyzed by the enzyme is the same for every nucleotide sequence, the equimolarity should be preserved. If this is the case, because the sequencing procedure is essentially a sampling process where the sample size is very large ($>10^7$) and the frequencies are very low, the observed number of counts should be well approximated by a Poisson distribution. That is, the number of distinct nucleotide sequences that are sequenced k times should be approximately equal to:

$$\frac{\lambda^k}{k!} \cdot e^{-\lambda}$$

where λ is equal to the ratio between the total number of sequences read and the number of possible sequences. By means of a $\chi^2$-test it is possible to test this hypothesis. For all the libraries of size 9 the p-value of this test was below $10^{-15}$, for libraries of size 21 prepared with ligase and standard adaptors the p-value was below $10^{-15}$, for libraries prepared only with PCR and libraries prepared with ligase and HD adaptors the p-value was greater than 0.2. Thus, the method demonstrates that the enzyme does not have the same efficiency for every nucleotide sequence.

DNA polymerase is probably the most important enzyme used in molecular biology as it is essential for PCR. Understanding the sequence preferences of DNA polymerase will help improve its efficiency. A degenerate oligonucleotide was used to study Phusion® DNA polymerase sequence preferences. A DNA oligonucleotide was designed that incorporated a degenerate region (9 nt or 21 nt) flanked by adaptor sequences required for Illumina sequencing. This sequence was amplified using Phusion® DNA polymerase for 15 cycles and the corresponding 100 nt band was gel extracted and sequenced using standard Illumina techniques. It was found that for the randomised 9mer, 99.5% of all possible sequences were identified but many were either over or under-represented. Similarly, many sequences were over-represented in the 21 mer sample (FIG. 2A, no ligation).

Figure 9:
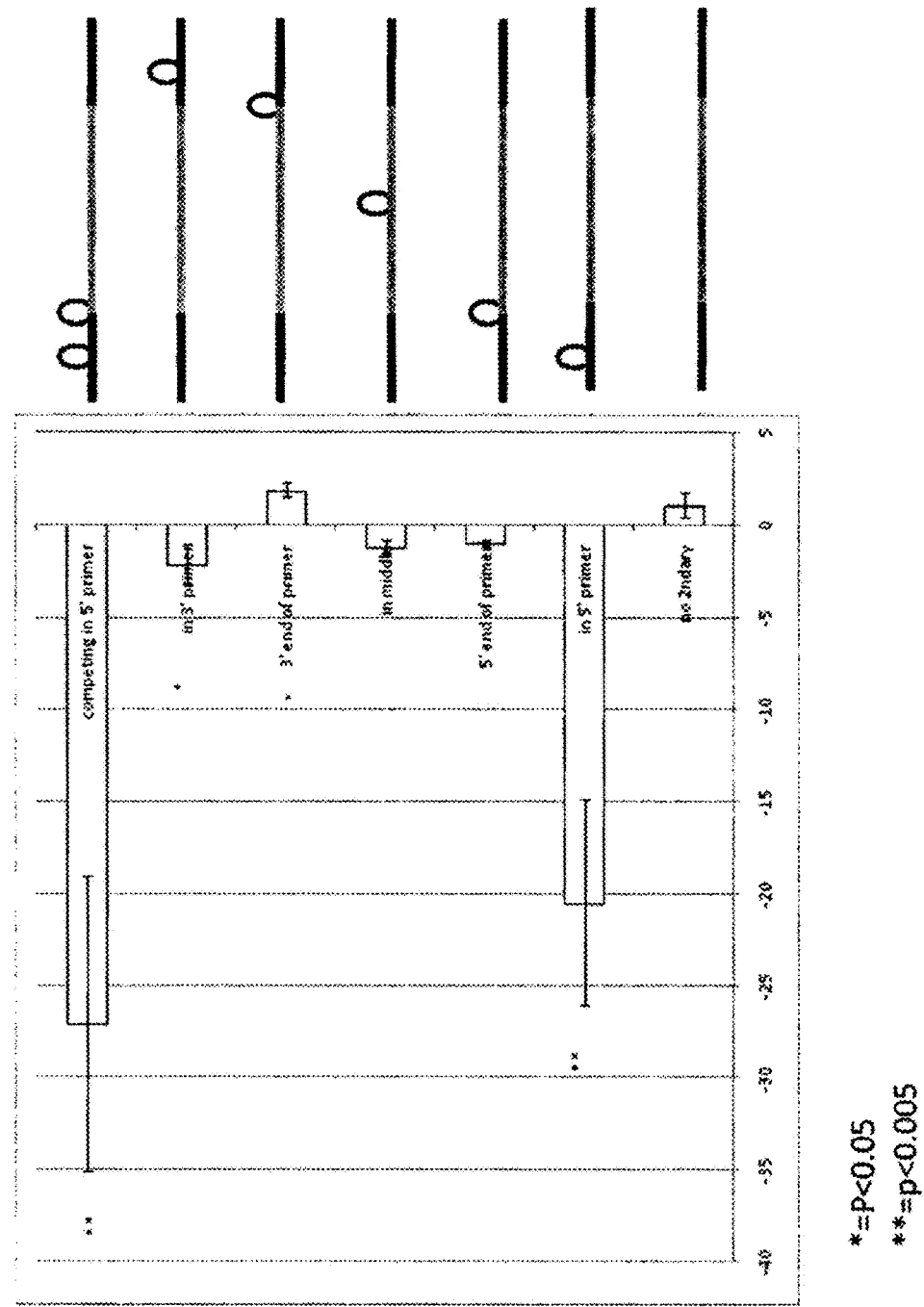
FIG. 9. Hairpin structures at the 3' end of the reverse primer preferred in qPCR experiments using Taq polymerase. Various DNA templates were synthesised that either had no strong predicted secondary structure or had predicted secondary structures at positions either in the priming sites at the ends of the primer sites or in between the priming sites. Since the templates were added in equimolar amounts the QPCR results show PCR efficiency. QPCR was more efficient for the template with a hairpin at the 3' end of the reverse primer. The templates were quantified spectophotometrically in triplicate and dilutions made equimolar. Dilutions of template were made in triplicate (n=3) with up to four technical replicates.

There was a strong correlation between the secondary structure of the single stranded PCR product and read counts for the N9 and N21 samples. Compared to control samples (bottom 10,000 read sequences for N9 and randomly generated for the 21 N samples) Phusion® polymerase preferred a hairpin structure at the end of the 3' end of reverse primer (FIG. 8). This preference was confirmed by using synthesised oligonucleotide templates with hairpins at various positions. QPCR was used to measure the activity of Taq polymerase. As expected the presence of a hairpin in the primer site for either the forward or reverse primers significantly reduced Taq polymerase activity. However, Taq polymerase was more efficient for the sequence with a hairpin at the primer site of the 5' end of the 3' primer (FIG. 9).

The reduction of PCR efficiency by secondary structures in the primer region has been described as a phenomenon but experimental evidence is lacking (Hoebeeck, van der Luijt et al. 2005). This work provides the first comprehensive evidence that secondary structures at the primer site is detrimental to PCR. Based on these observations it is envisaged that engineering stem loops into the 5' ends of 3' primer sites could be used to optimise PCR efficiency.

The methods described herein were also used to investigate the functional requirements for RNA Ligase 1 and 2. RNA ligases are dependent on the secondary structure context at the ligation site. T4 RNA ligase1 favours single stranded RNA. Truncated T4 RNA ligase2 can ligate single or double stranded RNA but is thought to prefer double stranded (Yin, Ho et al. 2003; Nandakumar, Ho et al. 2004). The secondary structure preference of T4 RNA ligase1 and truncated T4 RNA ligase2 was analysed. A degenerate 21 oligonucleotide was ligated to the 3' HD adaptor followed by ligation of the 5' HD adaptor. The most cloned sequences represent the preferred secondary structure for the activity of RNA ligase.

Figure 10:
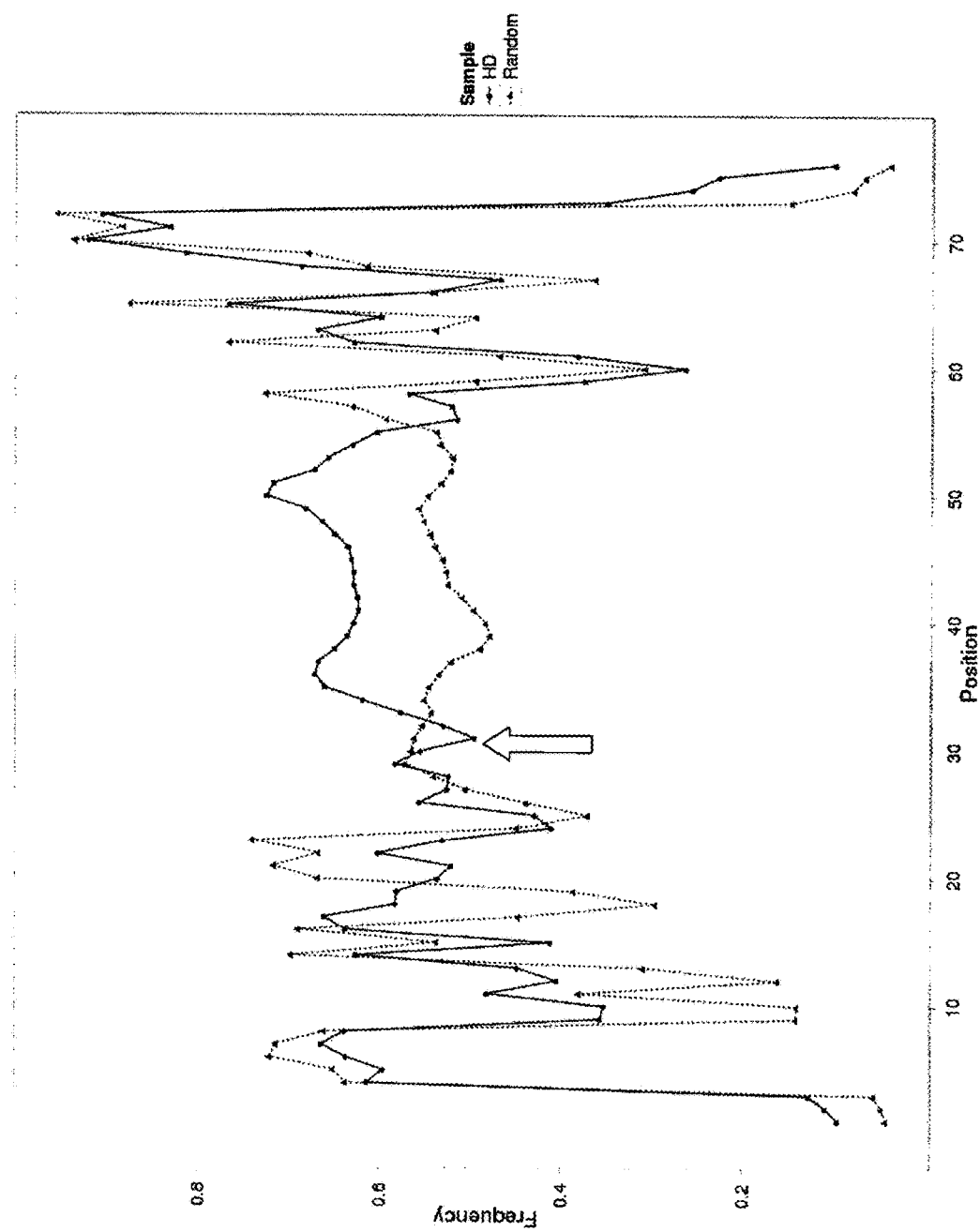
FIG. 10. Frequency of predicted nucleotide base-pairing per position for N21 sample. Solid line and circles represent set of sequences found two or more times in the HD dataset; dashed lines and triangles represent set of 5,000 randomly generated sequences. A. Sequence containing insert and 3' adaptor. B. Sequence containing 5' adaptor, insert and 3' adaptor. Arrows indicate ligation point.
Figure 10:
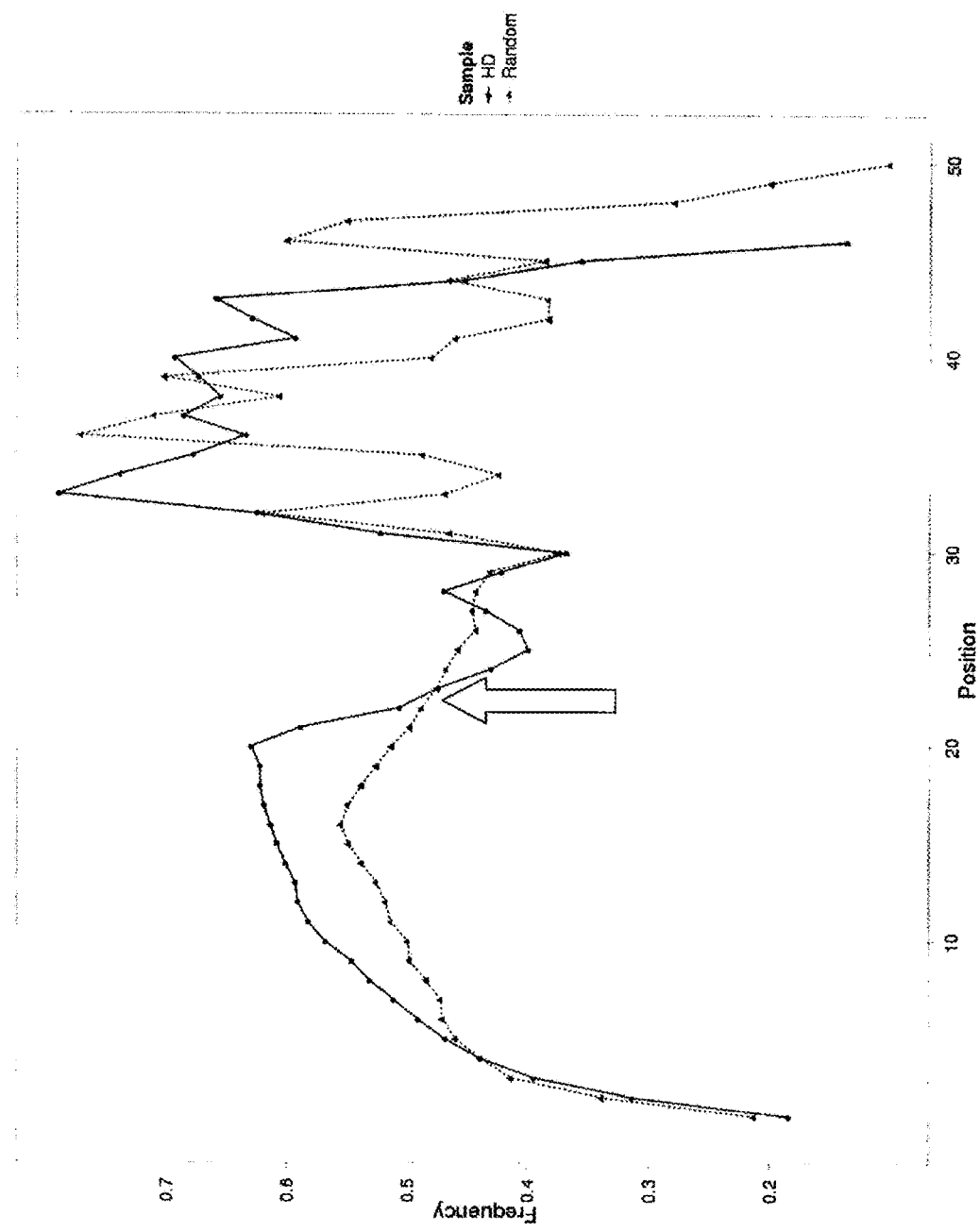

To analyse the secondary structure preference of the second ligation a control data set was generated by computationally folding 10,000 randomised 29mer oligonucleotides together with the 5' and 3' HD adaptors using RNA fold (Hofacker 2003). It was found that the ligation sites of RNA ligase1 or flanking regions had no distinctive preference for single stranded or double stranded RNA (FIG. 10A). The secondary structure from the top 5,000 read sequences including the 5' and 3' HD adaptor sequences were generated. A shift in the secondary structures at the flanking regions of the ligation site was found. Sequences that generated single stranded loop structures and 5' and 3' duplex stems were preferentially sequenced. This suggests that the activity of RNAligase1 prefers single stranded loops, which is similar to its in vivo role for the repair of the cleaved loop of tRNA-lys and therefore supports the validity of this approach (Amitsur, Levitz et al. 1987).

To analyse the secondary structure preference of the first ligation that uses truncated T4 RNA ligase2 a control data set was generated by computationally folding 10,000 randomised 25mer oligonucleotides together with the 3' HD adaptors using RNA fold. It was that the ligation sites of truncated T4 RNA ligase2 had no distinctive preference for single stranded or double stranded RNA (FIG. 10B). The secondary structure from the top 5,000 read sequences including the 5' and 3' HD adaptor sequences was then generated. It was found that the secondary structures flanking the ligation were distorted from the randomised data set. Sequences that generated 5' duplex structures and 3' single stranded structures with respect to the ligation site, and where the ligation site was situated in a loop, were preferentially sequenced. This suggests that the activity of truncated T4 RNA ligase2 prefers 3' duplex sequences but 5' single stranded regions. The current thinking is that RNA ligase2 seals nicks in double stranded RNA where the 5' and 3' regions of the ligation site would be double stranded. It is certainly true that RNA ligase2 can efficiently ligate nicks in double stranded RNA however it was initially shown that it can ligate single looped sequences (Yin, Ho et al. 2003). In addition our analysis is more in keeping with the proposed in vivo function of RNA ligase2 editing complex of Trypanasome that prefers single stranded residues at the ligation site (Cruz-Reyes, Zhelonkina et al. 2001).

The use of degenerate oligonucleotides to study protein function is not new. Randomised oligonucleotides are used in SELEX approaches to identify ligands for proteins. However this approach requires several rounds of selection and enrichment and does not identify activity determinants (Tuerk and Gold 1990). This is the first work that uses the Functional Analysis by Next Generation Sequencing (FANGS) method to directly investigate the function of a protein. It is envisaged that the FANGS method can be used to study many other nucleic acid modifying proteins such as reverse transcriptase, nucleic acid kinases and phosphatases and perhaps gyrases.

The present invention is not to be limited in scope by the specific aspects and embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments described herein are considered to be broadly applicable and combinable with any and all other consistent aspects and embodiments, as appropriate.

Various publications are cited herein, the disclosures of which are incorporated by reference in their entireties.

REFERENCES

Amitsur, M., R. Levitz, et al. (1987). "Bacteriophage T4 anticodon nuclease, polynucleotide kinase and RNA ligase reprocess the host lysine tRNA."*EMBO J* 6(8): 2499-2503.

Benes, V. and M. Castoldi (2010). "Expression profiling of microRNA using real-time quantitative PCR, how to use it and what is available." *Methods* 50(4): 244-249.

Cruz-Reyes, J., A. Zhelonkina, et al. (2001). "Trypanosome RNA editing: simple guide RNA features enhance U deletion 100-fold." *Mol Cell Biol* 21(3): 884-892.

Dalmay, T. (2008). "Identification of genes targeted by microRNAs." *Biochemical Society Transactions* 36(part 6): 1194-1196.

Dohm, J. C., C. Lottaz, et al. (2008). "Substantial biases in ultra-short read data sets from high-throughput DNA sequencing." *Nucleic acids research* 36(16): e105.

Fernandez-Valverde, S. L., R. J. Taft, et al. (2010). "Dynamic isomiR regulation in Drosophila development." *RNA* 16(10): 1881.

Fire, A., S. Xu, et al. (1998). "Potent and specific genetic interference by double-stranded RNA in *Caenorhabditis elegans*." *Nature* 391(6669): 806-811.

Guo, L. and Z. Lu (2010). "Global expression analysis of miRNA gene cluster and family based on isomiRs from deep sequencing data." *Computational Biology and Chemistry* 34(3): 165-171.

Hafner, M., et al. (2011). "RNA-ligase-dependent biases in miRNA representation in deep-sequenced small RNA cDNA libraries." *RNA* July 20 [Epub ahead of print].

Hansen, K. D., S. E. Brenner, et al. (2010). "Biases in Illumina transcriptome sequencing caused by random hexamer priming." *Nucleic acids research* 38(12): e131.

Harismendy, O., P. C. Ng, et al. (2009). "Evaluation of next generation sequencing platforms for population targeted sequencing studies." *Genome Biol* 10(3): R32.

Hoebeeck, J., R. van der Luijt, et al. (2005). "Rapid detection of VHL exon deletions using real-time quantitative PCR." *Lab Invest* 85(1): 24-33.

Hofacker, I. L. (2003). "Vienna RNA secondary structure server." *Nucleic Acids Res* 31(13): 3429-3431.

Linsen, S. E., E. de Wit, et al. (2009). "Limitations and possibilities of small RNA digital gene expression profiling." *Nat Methods* 6(7): 474-476.

McCormick, K. P., M. R. Willmann, et al (2011). "Experimental design, preprocessing, normalization and differential expression analysis of small RNA sequencing experiments." *Silence* 2(1): 2.

Moxon, S. et al (2008). "A toolkit for analysing large-scale plant small RNA datasets." *Bioinformatics* 24(19): 2252-2253

Nandakumar, J., C. K. Ho, et al. (2004). "RNA substrate specificity and structure-guided mutational analysis of bacteriophage T4 RNA ligase 2." *J Biol Chem* 279(30): 31337-31347.

Nandakumar, J. and Shuman S. (2004). "How an RNA ligase discriminates RNA versus DNA damage." *Mol Cell.* 16(2): 211-21

Oshlack, A. and M. J. Wakefield (2009). "Transcript length bias in RNA-seq data confounds systems biology." *Biology Direct* 4(1): 14.

Starega-Roslan, J., J. Krol, et al. (2011). "Structural basis of microRNA length variety." *Nucleic acids research* 39(1): 257.

Tian, G., X. Yin, et al. (2010) "Sequencing bias: comparison of different protocols of microRNA library construction." *BMC Biotechnol* 10: 64.

Tuerk, C. and L. Gold (1990). "Systematic evolution of ligands by exponential enrichment: RNA ligands to bacteriophage T4 DNA polymerase." *Science* 249(4968): 505-510.

Voinnet, 0. (2002). "RNA silencing: small RNAs as ubiquitous regulators of gene expression." *Curr Opin Plant Biol* 5(5): 444-451.

Willenbrock, H., J. Salomon, et al. (2009). "Quantitative miRNA expression analysis: comparing microarrays with next-generation sequencing." *RNA* 15(11): 2028-2034.

Yin, S., C. K. Ho, et al. (2003). "Structure-function analysis of T4 RNA ligase 2." *J Biol Chem* 278(20): 17601-17608.

The invention claimed is:

1. A method of reducing the sequence bias of a sequencing technique involving adaptor ligation, the method comprising:
   (a) providing a set of single-stranded oligonucleotides of known sequence with blocked 3' ends (3' adaptor molecules) and a set of single-stranded oligonucleotides of known sequence with blocked 5' ends (5' adaptor molecules), wherein the 3' and 5' adaptor molecules comprise two or more degenerate nucleotides grouped at the central region of the oligonucleotide wherein the 5' terminus of the 3' adaptor molecules and the 3' terminus of the 5' adaptor molecules are not degenerate;
   (b) ligating the 3' adaptor molecules to the 3' ends of the target nucleic acid molecules using a ligase, wherein the target nucleic acid molecules are RNA molecules;
   (c) ligating the 5' adaptor molecules to the 5' ends of the target nucleic acid molecules from step (b) using a ligase; and
   (d) determining the sequence of the target nucleic acid molecules obtained in step (c) using a primer capable of hybridising to the complement of the 5' adaptor molecule and a primer capable of hybridising to the 3' adaptor molecule.

2. The method according to claim 1, wherein the target nucleic acid is associated with a disease or pre-disease state, with a particular organism, with a particular tissue type, or with a particular developmental stage.

* * * * *